(12) United States Patent
Bloembergen et al.

(10) Patent No.: US 10,285,943 B2
(45) Date of Patent: *May 14, 2019

(54) APTAMER BIOCONJUGATE DRUG DELIVERY DEVICE

(75) Inventors: Steven Bloembergen, Okemos, MI (US); Ian J. McLennan, Burlington (CA); Nathan Jones, Hamilton (CA); Ryan Wagner, Kitchener (CA); Aareet Krsna Ganesh Shermon, Waterloo (CA); Abdel Rahman Elsayed, Waterloo (CA); Juewen Liu, Kitchener (CA)

(73) Assignee: GreenMark Biomedical Inc., East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/990,278

(22) PCT Filed: Dec. 2, 2011

(86) PCT No.: PCT/US2011/063102
§ 371 (c)(1),
(2), (4) Date: Aug. 21, 2013

(87) PCT Pub. No.: WO2012/075414
PCT Pub. Date: Jun. 7, 2012

(65) Prior Publication Data
US 2013/0337065 A1 Dec. 19, 2013

Related U.S. Application Data

(60) Provisional application No. 61/419,106, filed on Dec. 2, 2010.

(51) Int. Cl.
| | |
|---|---|
| *A61K 9/14* | (2006.01) |
| *A61K 9/51* | (2006.01) |
| *B82Y 5/00* | (2011.01) |
| *C08B 31/00* | (2006.01) |
| *A61K 9/16* | (2006.01) |
| *C08B 31/18* | (2006.01) |
| *C08B 33/00* | (2006.01) |
| *C08B 35/00* | (2006.01) |
| *A61K 31/704* | (2006.01) |
| *A61K 47/54* | (2017.01) |
| *A61K 47/69* | (2017.01) |
| *A61K 47/36* | (2006.01) |

(52) U.S. Cl.
CPC ............ *A61K 9/145* (2013.01); *A61K 9/1676* (2013.01); *A61K 9/5161* (2013.01); *A61K 31/704* (2013.01); *A61K 47/549* (2017.08); *A61K 47/6939* (2017.08); *B82Y 5/00* (2013.01); *C08B 31/003* (2013.01); *C08B 31/185* (2013.01); *C08B 33/00* (2013.01); *C08B 35/00* (2013.01); *A61K 47/36* (2013.01); *Y10S 977/773* (2013.01); *Y10S 977/906* (2013.01); *Y10T 428/2982* (2015.01)

(58) Field of Classification Search
CPC ............ A61K 49/0457; A61K 49/0073; A61K 49/1803; A61K 51/1203; A61K 9/14; A61K 9/15
See application file for complete search history.

(56) References Cited

U.S. PATENT DOCUMENTS

| | | |
|---|---|---|
| 2,148,951 A | 2/1939 | Maxwell |
| 2,328,537 A | 9/1943 | Felton et al. |
| 2,500,950 A | 3/1950 | Konigsberg |
| 2,801,242 A | 7/1957 | Kerr et al. |
| 2,929,811 A | 3/1960 | Hofreiter et al. |
| 2,989,521 A | 6/1961 | Senti et al. |
| 4,126,669 A | 11/1978 | Rothman et al. |
| 5,087,649 A | 2/1992 | Wegner et al. |
| 6,011,092 A | 1/2000 | Seppaelae et al. |

(Continued)

FOREIGN PATENT DOCUMENTS

| | | |
|---|---|---|
| EP | 0311873 A2 | 4/1989 |
| GB | 1420392 | 1/1976 |

(Continued)

OTHER PUBLICATIONS

M Hamidi, A Azidi, P Rafiei. "Hydrogel Nanoparticles in Drug Delivery." Advanced Drug Delivery Reviews, vol. 60, 2008, pp. 1638-1649.*
Ed Barker. "The Synthesis and Characterization of a Novel Polysaccharide Hydrogel for Biomedical Applications Including the Treatment of Malignant Tumors and the Prevention of Metastatic Disease." Thesis, University of Tennessee at Knoxville, Aug. 2007, pp. i-viii and 1-142 (150 total sheets).*
X Ma, R Jian, PR Chang, J Yu. "Fabrication and Characterization of Citric Acid-Modified Starch Nanoparticles/Plasticized-Starch Composites." Biomacromolecules, vol. 9, 2008, pp. 3314-3320.*

(Continued)

*Primary Examiner* — Isaac Shomer

(57) ABSTRACT

A delivery device for an active agent comprises nanoparticles based on a biopolymer such as starch. The delivery device may also be in the form of an aptamer-biopolymer-active agent conjugate wherein the aptamer targets the device for the treatment of specific disorders. The nanoparticles may be made by applying a high shear force in the presence of a crosslinker. The particles may be predominantly in the range of 50-150 nm and form a colloidal dispersion of crosslinked hydrogel particles in water. The biopolymer may be functionalized. The aptamer may be conjugated directly to the cross-linked biopolymers. The active agent may be a drug useful for the treatment of cancer. The delivery device survives for a period of time in the body sufficient to allow for the sustained release of a drug and for the transportation and uptake of the conjugate into targeted cells. However, the biopolymer is biocompatible and resorbable.

13 Claims, 8 Drawing Sheets

Specification includes a Sequence Listing.

(56) References Cited

U.S. PATENT DOCUMENTS

| | | | |
|---|---|---|---|
| 6,340,527 B1 | 1/2002 | Van Soest et al. | |
| 6,379,494 B1 | 4/2002 | Jewell et al. | |
| 6,677,386 B1 * | 1/2004 | Giezen | C08B 30/12 106/206.1 |
| 6,749,868 B1 | 6/2004 | Desai et al. | |
| 6,755,915 B1 | 6/2004 | Van Soest et al. | |
| 6,825,252 B2 | 11/2004 | Helbling et al. | |
| 6,921,430 B2 | 7/2005 | Bloembergen et al. | |
| 7,550,441 B2 | 6/2009 | Farokhzad et al. | |
| 8,043,480 B2 | 11/2011 | Lahann et al. | |
| 8,048,453 B1 | 11/2011 | Sung et al. | |
| 8,759,322 B2 | 6/2014 | Akiyoshi et al. | |
| 2002/0136769 A1 * | 9/2002 | Kabanov et al. | 424/487 |
| 2003/0219785 A1 | 11/2003 | Hallahan et al. | |
| 2004/0028745 A1 | 2/2004 | Bouhadir et al. | |
| 2004/0126900 A1 | 7/2004 | Barry et al. | |
| 2004/0241382 A1 | 12/2004 | Bloembergen et al. | |
| 2005/0191359 A1 | 9/2005 | Goldshtein et al. | |
| 2006/0002852 A1 | 1/2006 | Saltzman et al. | |
| 2006/0292280 A1 | 12/2006 | Soper et al. | |
| 2007/0224280 A1 | 9/2007 | Lillard et al. | |
| 2008/0081074 A1 * | 4/2008 | Gu | A61K 9/5153 424/489 |
| 2008/0233200 A1 | 9/2008 | Sung et al. | |
| 2008/0241257 A1 | 10/2008 | Popescu et al. | |
| 2009/0061010 A1 | 3/2009 | Zale et al. | |
| 2009/0117549 A1 | 5/2009 | Tan et al. | |
| 2009/0155409 A1 | 6/2009 | Sexton et al. | |
| 2009/0196831 A1 | 8/2009 | Yang et al. | |
| 2009/0226521 A1 | 9/2009 | Smyth et al. | |
| 2009/0312402 A1 | 12/2009 | Contag et al. | |
| 2010/0093659 A1 | 4/2010 | Natunen et al. | |
| 2010/0143738 A1 | 6/2010 | Bloembergen et al. | |
| 2010/0166872 A1 | 7/2010 | Singh et al. | |
| 2010/0266491 A1 | 10/2010 | Farokhzad et al. | |
| 2010/0272639 A1 | 10/2010 | Dutcher et al. | |
| 2011/0014296 A1 | 1/2011 | Chen et al. | |
| 2011/0038939 A1 | 2/2011 | Lvov et al. | |
| 2011/0042841 A1 | 2/2011 | Wildi et al. | |
| 2011/0244044 A1 | 10/2011 | Rossi et al. | |
| 2011/0244048 A1 | 10/2011 | Amiji et al. | |
| 2012/0141551 A1 | 7/2012 | Bloembergen et al. | |

FOREIGN PATENT DOCUMENTS

| | | | |
|---|---|---|---|
| JP | 2002544335 A | 12/2002 | |
| JP | 2004500438 A | 1/2004 | |
| JP | 2005535604 A | 11/2005 | |
| WO | 0069916 | 1/2000 | |
| WO | 0040617 A1 | 7/2000 | |
| WO | 0178786 A2 | 10/2001 | |
| WO | 03010206 A1 | 2/2003 | |
| WO | 03101425 A2 | 12/2003 | |
| WO | 2005108471 A1 | 11/2005 | |
| WO | 2007069272 A2 | 6/2007 | |
| WO | 2008022127 A2 | 2/2008 | |
| WO | 2008060575 A2 | 5/2008 | |
| WO | 2009146147 A2 | 12/2009 | |
| WO | 2010042823 | 4/2010 | |
| WO | 2010053140 A1 | 5/2010 | |
| WO | 2010065750 | 6/2010 | |
| WO | 2010080557 | 7/2010 | |
| WO | 2010084088 | 7/2010 | |
| WO | WO 2010084088 A2 * | 7/2010 | A61K 9/5161 |
| WO | 2011071742 | 6/2011 | |
| WO | 2011155979 | 12/2011 | |
| WO | 2012075414 | 6/2012 | |
| WO | 2012162845 A1 | 12/2012 | |

OTHER PUBLICATIONS

S Xiao, C Tong, L Xuanming, D Yu, Q Liu, C Xue, D Tang, L Zhao. "Preparation of folate-conjugated starch nanoparticles and its application to tumor-targeted drug delivery vector." Chinese Science Bulletin, vol. 51 No. 14, 2006, pp. 1693-1697.*

Patent Trial and Appeal Board. Ex Parte Podack. Appeal No. 2014-006893. Nov. 14, 2016. pp. 1-14 and a title page (15 total sheets).*

C Thiele, D Auerbach, G Jung, L Qiong, M Schneider, G Wenz. "Nanoparticles of anionic starch and cationic cyclodextrin derivatives for the targeted delivery of drugs." Polymer Chemistry, vol. 2, 2011, pp. 209-215, published online Oct. 23, 2010.*

D Le Corre, J Bras, A Dufresne. "Starch Nanoparticles: A Review." Biomacromolecules, vol. 11, 2010, pp. 1139-1153, published on web Apr. 20, 2010.*

De Le Corre, J Bras, A Dufresne. "Starch Nanoparticles: A Review." Biomacromolecules, vol. 11, 2010, pp. 1139-1153. Published on web Apr. 20, 2010. (Year: 2010).*

Herr, J.K., et al., "Aptamer-conjugated nanoparticles for selective collection and detection of cancer cells"., Anal. Chem., 2006, pp. 2918-2924, vol. 78, No. 9.

Ozalp, V.C., et al, "Aptamer-Gated Nanoparticles for Smart Drug Delivery", Pharmaceuticals, 2011, pp. 1137-1157, vol. 4.

Bates, P.J. et al., "Discovery and Development of the G-richOligonucleotide AS1411 as a Novel Treatment for Cancer", Exp. Mol. Pathol., 2009, pp. 151-164, vol. 86, No. 3.

Soundararjan, S., et al., "Plasma Membrane Nucleolin is a Receptor for an Anticancer Aptamer AS1411 in MV4-11 Leukemia Cells", Molecular Pharmacology, 2009, pp. 984-991, vol. 76, No. 5.

Peng, X.H., et al., "Targeted magnetic iron oxide nanoparticles for tumor imaging and therapy", International Journal of Nanomedicine, 2008, pp. 311-321, vol. 3, No. 3.

Farokhzad, O.C., "Nanoparticle-Aptamer Bioconjugates: A new Approach for Targeting Prostate Cancer Cells", Cancer Research, 2004, pp. 7668-7672, vol. 64.

International Search Report of PCT/US2012/056582, dated Feb. 28, 2013.

Saenger, W. V., "Cyclodextrin-Einschubverbindungen in Forschung ung Industrie", Angew. Chem., 1980, pp. 343-361, vol. 92, In German.

Wenz, G., "Cyclodextrine als Bausteine supramolekularer Strukturen and Funktionseinten", Angew. Chem. 1994, vol. 106, pp. 851-870, In German.

Bloembergen, S., et al., "Specialty Biobased Monomers and Emulsion Polymers Derived from Starch", Presented to the PTS Advanced Coating Fundamentals Symposium, Munich, Germany, Oct. 11-14, 2010, pp. 1-19.

Bloembergen, S., et al., "Biolatex Binders for Paper and Paperboard Applications", Journal of Pulp and Paper Science, 2010, pp. 1-11, vol. 36, No. 3-4.

Shangguan, D., "Aptamers Evolved from Cultured Cancer Cells Reveal Molecular Differences of Cancer Cells in Patient Samples", Clinical Chemistry, 2007, pp. 1-3, vol. 53, No. 6.

Lai, P.S., et al., "AS1411 aptamer-conjugated polymeric micelle for targetable cancer therapy", Nanotech Conference & Expo 2010, Jun. 21-24, 2010, Anaheim, CA, Abstract, 1 page.

Stuart, R.K., et al., "Randomized phase II trial of the nucleolin targeting aptamer AS1411 combined with high-dose cytarabine in relapsed/refractpry acute myeloid leukemia (AML)", J. Clin. Oncol., 2009, vol. 27(15s), Abstract, 3 pages.

Mongelard, F. And Bouvet, P., "AS-1411, a guanosine-rich oligonucleotide aptamer targeting nucleolin for the potential treatment of cancer, including acute myeloid leukemia", Curr. Opin. Mol. Ther., 2010, pp. 107-114, vol. 12(1), Abstract, 1 page.

International Search Report of PCT/US2011/063102, dated Jul. 6, 2012.

Shin, J.Y., et al., "Rheological properties of starch latex dispersions and starch latex-containing coating colors", Presented at PaperCon 2012, "Growing the Future", New Orleans, LA, Apr. 21-25, 2012, pp. 1-26.

Jones, N., et al., "Targeted Starch Nanoparticles for Cancer Therapy", Design Symposium, Mar. 23, 2012, 1 page.

Song et al., "Starch nanoparticle formation via reactive extrusion and related mechanism study", Carbohydrate Polymers, 2011, vol. 85, pp. 208-214.

(56) References Cited

OTHER PUBLICATIONS

Bloembergen, et al., "Paper Binder Performance with Nanoparticle Biolatex™: EcoSynthetix develops EcoSphere® biolatex for replacement of petroleum based latex binders", ACFS, Montreal, Jun. 11-13, 2008, 9 pages.
Thiele, C. et al., "Nanoparticle of anionic starch and cationic cyclodextrin derivatives for the targeted delivery of drugs", Polym. Chem., 2011, vol. 2, pp. 209-215.
Xiao et al., "Preparation of folate-conjugated starch nanoparticles and its application to tumor-targeted drug delivery vector", Chinese Science Bulletin 2006 vol. 51 No. 14, pp. 1693-1697.
Fishman et al., "Molar masses and sizes of starches by high-performance size-exclusion chromatography with on-line multi-angle laser light scattering detection", J. Agric. Food Chem. 1996, 44, pp. 3182-3188.
Amin, S. et al. "Hydrogels as Potential Drug Delivery Systems", Scientific Research and Essay. 2009; 3(11): 1175-1183.
Aravind et al., "Aptamer-Labeled PLGA Nanoparticles for Targeting Cancer Cells," Cancer Nano, 2012, vol. 3, pp. 1-12.
Blank, Michael et al., Systematic Evolution of a DNA Aptamer Binding to Rat Brain Tumor Microvessels. Selective Targeting of Endothelial Regulatory Protein Pigpen., J. Biol. Chem. 276 (2001) 16464-16468.
Davis., et al., "The Reticulo-Endothelial System and Blood Clearance," Microspheres and Drug Therapy: Pharmaceutical, Immunological and Medical Aspects, Elsevier, New York, Chapter 2, Jan. 1984, pp. 25-37.
Examiner's Answer to Appeal Brief dated Aug. 6, 2015 in related U.S. Appl. No. 13/310,287.
Final Office Action dated Sep. 9, 2016 for U.S. Appl. No. 14/360,503, filed May 23, 2014.
Heidel, Jeremy D. et al. Cyclodextrin-Containing Polymers: Versatile Platforms of Drug Delivery Materials, Journal of Drug Delivery, vol. 2012.
International Preliminary Report on Patentability for Application No. PCT/US2011/063102, dated Jun. 4, 2013, 9 pages.
International Preliminary Report on Patentability for Application No. PCT/US20121056582, dated Jun. 3, 2014, 10 pages.
Jain, Akhlesh Kumar et al., Effective insulin delivery using starch nanoparticles as a potential trans-nasal—nucoadhesive carrier, European Journal of Pharmaceutics 69 (2008) 426-435.
Lee, Do Ik, et al., "Development of New Biobased Emulsion Binders", PaperCon2010, Talent, Technology and Transformation, Atlanta, GA, May 2-5, 2010; 46 pages.
Non-Final Office Action dated Jan. 22, 2016 for U.S. Appl. No. 14/360,503, filed May 23, 2014.
Office Action dated Aug. 10, 2015 for U.S. Appl. No. 14/360,503, filed May 23, 2014.
Office Action dated Apr. 3, 2014 in related U.S. Appl. No. 13/310,287.
Office Action dated Apr. 4, 2014 in related U.S. Appl. No. 13/614,120.
Office Action dated Dec. 8, 2014 in related U.S. Appl. No. 13/614,120.
Office Action dated Feb. 7, 2013 in related U.S. Appl. No. 13/614,120.
Office Action dated Jul. 18, 2013 in related U.S. Appl. No. 13/310,287.
Office Action dated Jul. 21, 2014 in related U.S. Appl. No. 13/310,287.
Office Action dated Jul. 24, 2014 in related U.S. Appl. No. 13/614,120.
Office Action dated Jul. 29, 2013 in related U.S. Appl. No. 13/614,120.
Office Action dated Jul. 5, 2012 in related U.S. Appl. No. 13/310,287.
Office Action dated Jun. 13, 2014 in related U.S. Appl. No. 13/614,120.
Office Action dated Jun. 16, 2014 in related U.S. Appl. No. 13/310,287.
Office Action dated Nov. 21, 2012 in related U.S. Appl. No. 13/310,287.
Office Action dated Oct. 31, 2013 in related U.S. Appl. No. 13/310,287.
Saboktakin, Mohammad Reza et al. pH-sensitive starch hydrogels via free radical graft copolymerization, synthesis and properties, Carbohydrate Polymers 77 (2009) 634-638.
Shangguan, D. et al., Aptamers evolved from live cells as effective molecular probes for cancer study, Proc Natl lead Sci U S A. Aug. 8, 2006;103(32):11838-43.
Simi, C.X., et al. Hydrophobic grafted and cross-linked starch nanoparticles for drug delivery, Bioprocess Biosyst Eng :2007, 30:173-180.
Supplementary Partial European Search Report for Application No. EP11845209, dated Jul. 29, 2016, 7 pages.
Written Opinion for Application No. PCT/US2011/063102, dated Jul. 6, 2012, 8 pages.
Written Opinion for Application No. PCT/US2012/056582, dated Feb. 28, 2013, 9 pages.
Wu, Yanrong et al., DNA aptamer-micelle as an efficient detection/delivery vehicle toward cancer cells, Proceedings of the National Academy of Sciences of the United States of America, vol. 107, No. 1, Jan. 5-10, 2010.
Xiao, Suyao et al., Studies of poly-L-lysine-starch nanoparticle preparation and its application as gene carrier, Science in China Ser. B Chemistry 2005 vol. 48 No. 2 162-166.
Alnis Biosciences Inc et al., English language abstract of JP2005-535604, published Nov. 24, 2005.
European Patent Application No. 11845209, Extended European Search Report dated Mar. 7, 2017. 6 pages.
Soontornworajit et al., "Aptamer-Functionalized in Situ Injectable Hydrogel for Controlled Protein Release," Journal of Biomacromolecules, Sep. 1, 2010, vol. 11 (10), pp. 2724-2730.
U.S. Appl. No. 13/310,287, Decision on Appeal dated Mar. 31, 2017. 12 pages.
European Patent Application No. 11845209.3, Office Action dated Nov. 21, 2017.
Canadian Patent Application No. 2,819,240, Examiner's Requisition dated Jan. 11, 2018.
U.S. Appl. No. 14/360,503, Non-Final Office Action dated Nov. 24, 2017.
Dave et al., "Regenerable DNA-Functionalized Hydrogels for Ultrasensitive, Instrument-Free Mercury(II) Detection and Removal in Water," Journal of the American Chemical Society, Aug. 2010, vol. 132 (36), pp. 12668-12673.
Farokhzad et al., "Nanoparticle-Aptamer Bioconjugates for Cancer Targeting," Expert Opinion on Drug Delivery, May 2006, vol. 3 (3), pp. 311-324.
Mangalam et al., "Cellulose/DNA Hybrid Nanomaterials," Biomacromolecules, Mar. 2009, vol. 10 (3), pp. 497-504.
Phillips et al., "Applications of Aptamers in Cancer Cell Biology," Analytica Chimica Acta, Jul. 2008, vol. 621 (2), pp. 101-108.
Shangguan et al., "Aptamers Evolved From Live Cells as Effective Molecular Probes for Cancer Study," Proceedings of the National Academy of Sciences, Aug. 2006, vol. 103 (32), pp. 11838-11843.
Nu et al., "DNA Aptamer-Micelle as an Efficient Detection/Delivery Vehicle Toward Cancer Cells," Proceedings of the National Academy of Sciences, Jan. 2010, vol. 107 (1), pp. 5-10.
European Patent Application No. 11845209.3, Office Action dated Oct. 24, 2018.
Canadian Patent Application No. 2,819,240, Office Action dated Sep. 26, 2018.
U.S. Appl. No. 14/360,503, Office Action dated Aug. 16, 2018.
Gu, Frank X. et al., "Targeted nanoparticles for cancer therapy", nanotoday, Jun. 2007, vol. 2, No. 3, pp. 14-21.

* cited by examiner

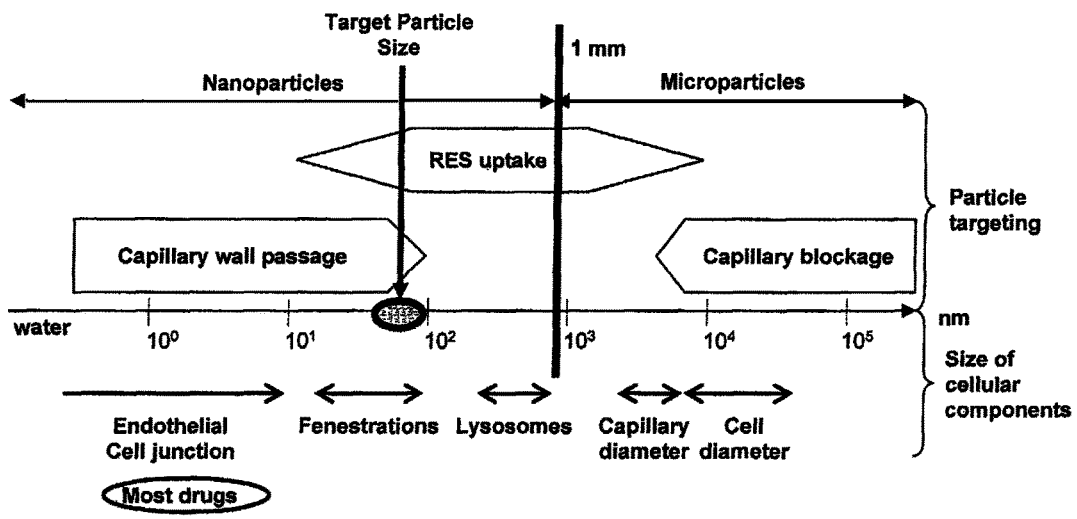
FIGURE 1
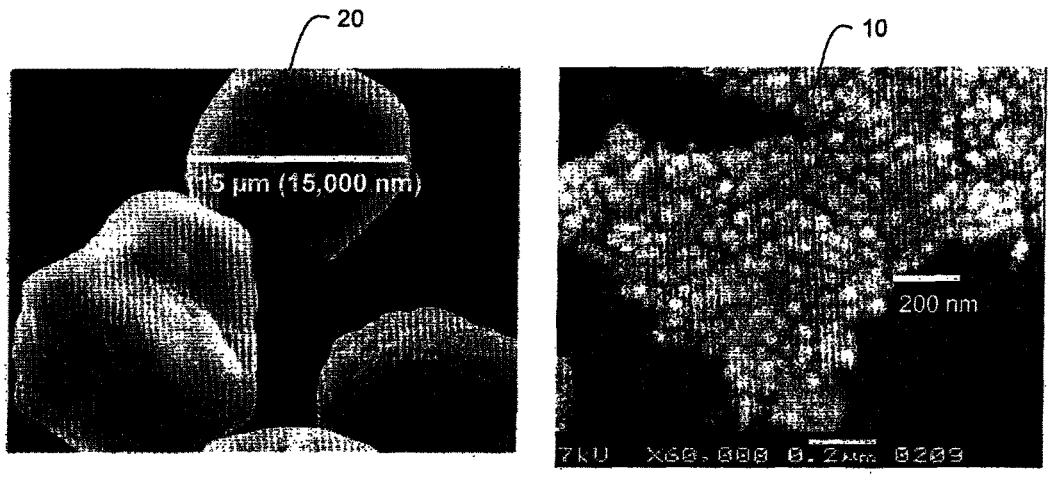
Native Starch Granules
FIGURE 2A
EcoSphere® 2202
FIGURE 2B

*Structure of a Carboxylated
SB Latex Particle*

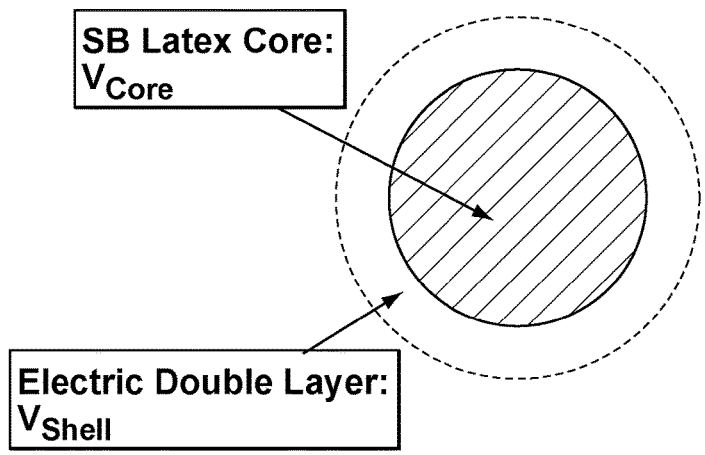

Since SB Latex particle cores are not swollen, the swell ratio is one:

$$V_{Core\text{-}swollen} / V_{Core\text{-}unswollen} = 1.0$$

FIGURE 6A

*Structure of a Water-Swollen,
Crosslinked Starch Nanoparticle*

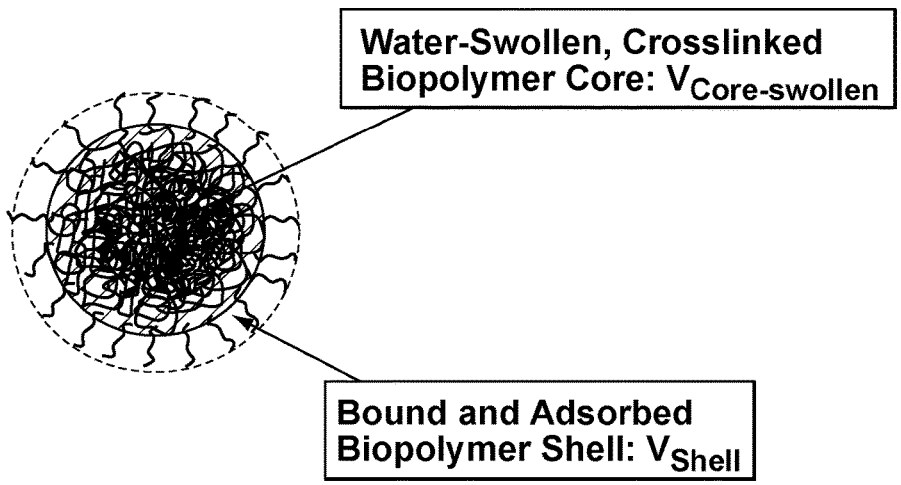

If $V_{shell}$ is assumed to be 2 times $V_{Core\text{-}swollen}$, then the swell ratio will become (at extreme dilution):

$$V_{Core\text{-}swollen} / V_{Core\text{-}unswollen} = 4.7$$

At 40% solids this swell ratio is:

$$V_{Core\text{-}swollen} / V_{Core\text{-}unswollen} = 2.5$$

FIGURE 6B

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Aptamer
<220> FEATURE:
<221> NAME/KEY: misc_feature
<222> LOCATION: (1)..(1)
<223> OTHER INFORMATION: 5' 6-carboxyfluorescein modified adenine
<220> FEATURE:
<221> NAME/KEY: misc_feature
<222> LOCATION: (24)..(24)
<223> OTHER INFORMATION: 3' amine modified guanine

<400> SEQUENCE: 1
acgcatctgt gaagagaacc tggg                                              24

<210> SEQ ID NO 2
<211> LENGTH: 28
<212> TYPE: DNA
<213> ORGANISM: Artificial Sequence
<220> FEATURE:
<223> OTHER INFORMATION: Aptamer AS1411
<220> FEATURE:
<221> NAME/KEY: misc_feature
<222> LOCATION: (1)..(1)
<223> OTHER INFORMATION: 5' cyanine-3 modified thymine
<220> FEATURE:
<221> NAME/KEY: misc_feature
```

-continued

```
<222> LOCATION: (28)..(28)
<223> OTHER INFORMATION: 3' amine modified guanine

<400> SEQUENCE: 2
ttggtggtgg tggttgtggt ggtggtgg                                            28
```

APTAMER BIOCONJUGATE DRUG DELIVERY DEVICE

CROSS REFERENCE TO RELATED APPLICATIONS

This application is a national phase entry of PCT/US2011/063102, filed on Dec. 2, 2011, which claims the benefit under 35 USC 119 of U.S. Provisional Application No. 61/419,106 filed on Dec. 2, 2010. PCT/CA2011/063102 and 61/419,106 are hereby incorporated by reference.

STATEMENT REGARDING FEDERALLY-SPONSORED RESEARCH OR DEVELOPMENT

Parts of this invention was made with government support under Small Business Innovation Research (SBIR) Flair Program grant, award number R43 CA 92817-02, called "Development of Drug Delivery Systems Based on New Bio-synthetic Hybrid Materials" awarded by National Institutes of Health (NIH) and National Cancer Institutes (NCI). The government has certain rights in the invention.

FIELD

This specification relates to a delivery device for drugs or other agents, to methods of making and using the delivery device, and to the treatment of cancer.

BACKGROUND

The following discussion is not an admission that anything described below is common general knowledge.

U.S. Pat. No. 6,340,527 to Van Soest et al. describes microparticles having a particle size of 50 nm to 1 mm consisting of a chemically cross-linked starch shell containing an active ingredient. The particles are obtained by first preparing an oil in water emulsion of the active ingredient in a hydrophobic phase and starch, or a dispersion of a solid active ingredient and starch in water. The active ingredient may be a medicament which is released in the digestive tract when the starch degrades.

U.S. Patent Application Publication U.S. 2008/0241257 to Popescu et al. describes a nanoparticle of a biodegradable polymer containing a hydrophilic cationic drug such as streptomycin. The biodegradable polymer may be chitosan. A pharmaceutical preparation containing the nanoparticles is administered to a patient orally and the nanoparticles release the drug in vivo. The drug can be complexed with a naturally occurring polymer, such as dextran sulfate. The drug, optionally complexed, is mixed with the biodegradable polymer followed by an inorganic polyanion to form the nanoparticle. In one example, the nanoparticles were about 560 nm in average size, had a zeta potential of about +54 mV and were used to treat tuberculosis in mice.

U.S. Pat. No. 7,550,441 to Farokhzad et al. describes a conjugate that includes a nucleic acid ligand bound to a controlled release polymer system contained within a pharmaceutical compound. Some examples of the polymer system are based on poly(lactic) acid (PLA) and have mean particle sizes ranging from 137 to 2805 nm. The ligands have an affinity for a target and are prepared through the Systemic Evolution of Ligands by Exponential Enrichment (SELEX) process.

U.S. Patent Publication 2009/0312402 to Contag et al. describes nanoparticles with encapsulated nucleic acid. The polymer may be PLA, PLG or PLGA and PEG. The particles may have ligands or antibodies attached to them for targeting the nanoparticles to a site of interest. The nanoparticles may have a polymer coating to provide controlled release. The particles are in the size range of about 50 nm to about 500 nm, with most of them in the sub-200 nm range.

U.S. Patent Publication 2011/0244048 to Amiji et al. describes a method of making a nanoparticle comprising combining an aqueous solution of a solubilized therapeutic agent with a water-soluble polymer comprising polyethylene glycol (PEG) and a fatty acid. These components self assemble into a nanoparticle. Various dextran based particles have means sizes ranging from 14 nm to 430 nm. The therapeutic agent may be doxorubicin.

U.S. Pat. No. 8,048,453 to Sung et al. describes nanoparticles of chitosan, poly-glutamic acid, and an active agent. The particles have a mean particle size between about 50 nm and 400 nm. The active agent may be insulin for the treatment of diabetes or an active for treating Alzheimer's disease. The nanoparticles may be freeze-dried and loaded into a capsule for oral administration.

INTRODUCTION TO THE INVENTION

The following introduction is intended to introduce the reader to the invention and the detailed description to follow and not to limit or define the claims.

This specification describes a nanoparticle based delivery device. The device may be used for the treatment of various indications or for other purposes. However, this specification will primarily describe the use of the device to deliver chemotherapeutic drugs to treat cancer.

The development of new and improved chemotherapeutic delivery devices is clearly important. Cancer is the second most common cause of death in the US, accounting for 1 of every 4 deaths. With solid tumor cancers, sufficiently localized tumors can be removed by a surgeon. In most cases, however, not all of the tumor is removed and follow-up therapy with radiation or chemotherapy is required. In the United States, about 50% of cancer patients will receive chemotherapy. With metastatic cancers that are widely disseminated upon diagnosis, such as leukemias, chemotherapy is required.

The delivery device described in this specification includes a nanoparticle that was originally developed as an industrial latex. In brief, the particle is made predominantly from a biopolymer, such as a starch comprising amylose or amylopectin or both, that has its crystal structure broken, for example by shear forces and intensive mixing in the presence of a hydroxilic solvent. After the crystal structures have been broken, a crosslinking agent is added. The resulting nanoparticles, comprising for example cross-linked high molecular weight starch polymers, can be handled as dry agglomerated particles and later dispersed in an aqueous medium to produce a stable latex dispersion of crosslinked hydrogel nanoparticles.

These particles have been used, for example, in papermaking slurries, as a binder in a pigmented paper coating composition, and as an adhesive. However, the inventors believe that these particles have attributes that make them useful as a drug delivery device. In an aqueous medium, the nanoparticles form a stable dispersion of swollen cross-linked biopolymer hydro-colloid particles. The particles swell by taking water into the core of the particle. This mechanism may be used to load a drug into the core of the particle while allowing the drug to be released later in the body of a person, or another mammal. The nanoparticles can be administered as a liquid suspension or dried to produce a powder.

One useful attribute of the nanoparticles is that they can be broken down by chemical and enzymatic elements, but they persist in the body long enough to give a sustained drug release. While native starch particles would survive for less than 30 minutes in the body, the crosslinked starch nanoparticles have a considerably longer half life. In a related attribute, the nanoparticles can provide two mechanisms for releasing an encapsulated drug. According to a first mechanism, the drug is released from a generally intact particle. According to a second mechanism, degradation of the particle releases more of the drug. This provides a sustained release of the drug, which is useful for therapeutic agents that require several hours or more of residence time within the body for the drug to act.

Another attribute of the nanoparticles is that the biopolymers are compatible with the body and ultimately resorbable. The biopolymers and their metabolites are non toxic and recognized by the body as foodstuff. In contrast, some synthetic polymers can cause side effects when used as a drug delivery device. For example, polyanhydride copolymers used for drug delivery have have been associated with tissue inflammation and an enhanced rate of infections, possibly because they degrade via hydrolysis and yield acidic functionalities. Starch, however, is ordinarily a food source and can be taken up by the body as it degrades essentially without complications.

Another useful attribute of the nanoparticles is their size, and their narrow particle size distribution which indicates a narrow range of particles sizes within a sample. In particular, the nanoparticles have sizes that are predominantly in the range of 50-150 nm. Particles outside of this size range are quickly removed from the body through capillary wall passage or by the reticuloendothelial system (RES).

Yet another useful attribute of the nanoparticles is that the biopolymers may be functionalized. For example, amylose and amylopectin molecules may be oxidized and provided with carboxyl functionalities. In this example, the functionalized particles have a more negative zeta potential which aids in the adsorption of some drugs and the attachment of targeting moieties such as a ligand. For example, a nucleotide such as an aptamer may be attached, for example via a carbodimide linkage, directly to the surface of a crosslinked structure forming the core of the particle. Other forms of functionalization may influence the attachment of a targeting molecule or the release profile of a drug.

A drug delivery device may take advantage of any one or more of these or other attributes. An example of a drug delivery device described in this specification comprises nanoparticles made predominantly of high molecular weight starch or cross-linked biopolymers and conjugated to an active agent such as a chemotherapeutic drug. The nanoparticles may be made by mixing under high shear forces and then adding a crosslinker. The nanoparticles are predominantly in the range of 50-150 nm in size and form a hydro-colloidal dispersion in water. Optionally, the nanoparticles, and in particular the crosslinked polymers, may be further conjugated to a targeting molecule such as an aptamer. The aptamer targets the nanoparticles for delivery of the active agent to cancer cells.

A drug delivery device may have: 1) a nanoparticle comprising crosslinked biocompatible or resorbable polymers, the polymers modified after the particle was formed by chemical or enzymatic modification, 2) an encapsulated active agent within the colloidal hydrogel, and, optionally, 3) an aptamer attached to the cross-linked polymers. The nanoparticles may be colloidal hydrogel particles.

A medicament described in this specification comprises a plurality of nanoparticles, the nanoparticles made up mostly of high molecular weight starch, with an active agent conjugated to at least some of the nanoparticles. The medicament may be useful in the treatment of cancer. A method of making a medicament comprises steps of forming a plurality of high molecular weight starch based nanoparticles, the nanoparticles having a size predominantly in the range of 50 to 150 nm, and combining a drug or other agent with a least some of nanoparticles.

A compound described in this specification comprises a high molecular weight starch based nanoparticle core having a size in the range of 50 to 150 nm, a therapeutic agent and an aptamer. The compound may be used for the treatment of cancer.

BRIEF DESCRIPTION OF THE DRAWINGS

FIG. 1 is a chart showing a target particle size relative to particle removal mechanisms.

FIG. 2 shows an electron microscopy comparison of native corn starch granules to EcoSphere® 2202 cross-linked starch nanoparticles.

FIG. 6 is a schematic representation of minor swelling in an SB latex particle and significant swelling of the cross-linked starch nanoparticles of FIG. 2 in an aqueous dispersion, illustrating the hydrocolloid structure of the starch based nanoparticles.

DETAILED DESCRIPTION

Target Particle Size

Figure 3:
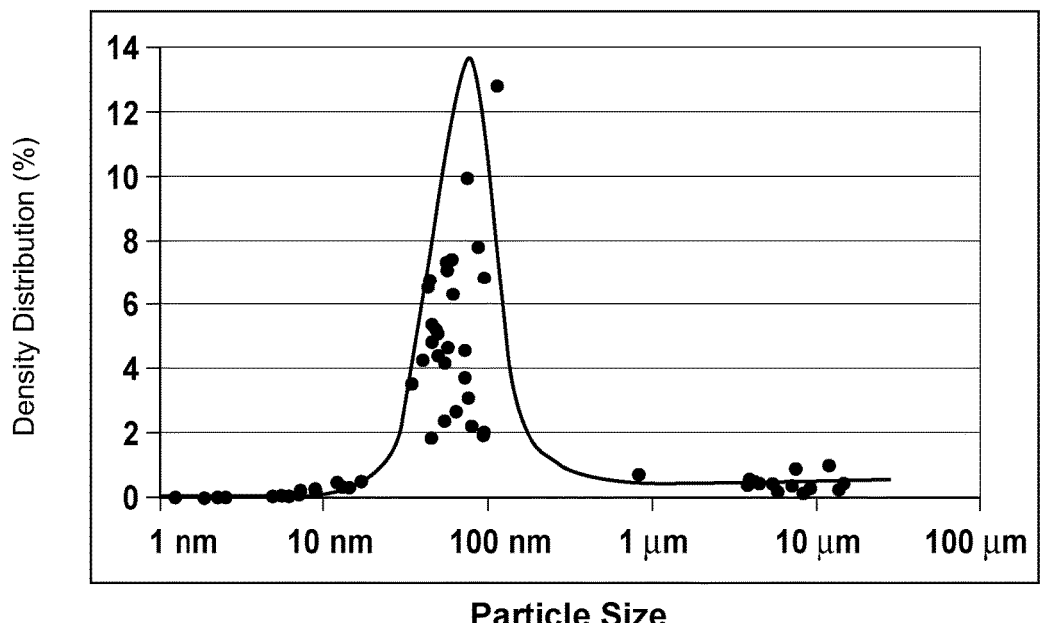
FIG. 3 shows an analysis of particle size for an aqueous dispersion of the cross-linked starch nanoparticles of FIG. 2 by Dynamic Laser Light Scattering (DLS).

Referring to FIG. 1, particle size plays a role in determining the fate of a drug or a drug delivery mechanism after administration. Microparticles, being particles of one micron or greater in size, are removed from the body within minutes by the pulmonary capillary system.

Nanoparticles (particles less than one micron in size), however, can be rapidly removed from the blood stream by phagocyctic cells of the reticular endothelial system (RES). (see for example Park, K., "Controlled Drug Delivery: Challenges and Strategies", American Chemical Society, Washington, D.C., 1997 and Davis, S. S., "Microspheres and Drug Therapy: Pharmaceutical, Immunological and Medical Aspects", Elsevier, New York, N.Y., USA, Chapter 2, 1984). In one study (Davis, 1984), upon administering colloid particles of poly(styrene) latex, the particles appeared in the Kupffer cells of the liver and subsequently in the spleen. Leakage of latex particles into the systemic system occurred for particles less than 100 nm, but particles of 200 to 500 nm in diameter were removed from the blood within 5 minutes.

Particles under 70 nm in size have been shown to be taken up through capillary wall passage and are quickly excreted by subjects. Accordingly, extremely small particles also do not have long systemic circulation. This includes most drugs and aptamers.

It is possible that particles in the range of about 50 to 100 nm in size are taken up through capillary wall passage and by the RES. However, both mechanisms may be only marginally effective against particles in this size range and up to about 150 nm. Without intending to be bound by any particular theory of operation, particles having a size in the range of about 50 to 150 nm enjoy longer systemic circulation as a result of being within this size range, independently of other properties of the particle such as surface density or hydrophilicity which may also affect uptake by the RES.

Biopolymer Nanoparticles

Biopolymer nanoparticles are made according to a process described in U.S. Pat. No. 6,677,386 (which corresponds to International Publication WO 00/69916). In the process, a biopolymer, such a starch comprising amylose or amylopectin or both, is combined with a plasticizer. This combination is mixed under high shear forces, preferably in a twin screw fully intermeshing co-rotating extruder, to plasticize the biopolymer and create a thermoplastic melt phase in which the crystalline structure of the biopolymer is removed. A crosslinking agent is then added while mixing continues to form cross-linked nanoparticles. The nanoparticles exit the extruder as a strand, which is ground to a fine dry powder. The starch based nanoparticles are present in the powder in agglomerated form, and can be dispersed in an aqueous medium.

The biopolymers may be starch or other polysaccharides such as cellulose and gums, as well as proteins (e.g. gelatin, whey protein). The biopolymers may be previously modified, e.g. with cationic groups, carboxy-methyl groups, by acylation, phosphorylation, hydroxyalkylation, oxidation and the like. Starch and mixtures of at least 50% starch with other polymers are preferred. The starch, whether used alone or in a mixture, is preferably a high molecular weight starch, for example a molecular weight of at least 10,000, and not dextran or dextrin. For example, the starch may be made up of amylose or amylopectin or both. Waxy starches, such as waxy corn starch, are particularly preferred.

The following five paragraphs are repeated or summarized from U.S. Pat. No. 6,677,386 to further describe the process of making the nanoparticles.

The biopolymer preferably has a dry substance content of at least 50% by weight at the time when processing starts. Processing is preferably done at a temperature of at least 40 degrees C., but below the degradation temperature of the polymer, for example 200 degrees C. The shear can be effected by applying at least 100 J of specific mechanical energy (SME) per g of biopolymer. Depending on the processing apparatus used the minimum energy may be higher; also when non-pregelatinised material is used, the minimum SME may be higher, e.g. at least 250 J/g, especially at least 500 J/g.

The plasticiser may water or a polyol (ethyleneglycol, propyleneglycol, polyglycols, glycerol, sugar alcohols, urea, citric acid esters, etc.). The total amount of plasticisers (i.e. water and others such as glycerol) is preferably between 15 and 50%. A lubricant, such as lecithin, other phospholipids or monoglycerides, may also be present, e.g. at a level of 0.5-2.5% by weight. An acid, preferably a solid or semi-solid organic acid, such as maleic acid, citric acid, oxalic, lactic, gluconic acid, or a carbohydrate-degrading enzyme, such as amylase, may be present at a level of 0.01-5% by weight of biopolymer. The acid or enzyme assists in slight depolymerisation which is assumed to be advantageous in the process of producing nanoparticles of a specific size.

The crosslinking is preferably reversible, i.e. the crosslinks are partly or wholly cleaved after the mechanical treatment step. Suitable reversible crosslinkers include those which form chemical bonds at low water concentrations, which dissociate or hydrolyse in the presence of higher water concentrations. This mode of crosslinking results in a temporary high viscosity during processing followed by a lower viscosity after processing. Examples of reversible crosslinkers are dialdehydes and polyaldehydes, which reversibly form hemiacetals, acid anhydrides and mixed anhydrides (e.g. succinic and acetic anhydride) and the like. Suitable dialdehydes and polyaldehydes are glutaraldehyde, glyoxal, periodate-oxidised carbohydrates, and the like. Glyoxal is a particularly suitable crosslinker.

Such crosslinkers may be used alone or as a mixture of reversible crosslinkers, or as a mixture of reversible and non-reversible crosslinkers. Thus, conventional crosslinkers such as epichlorohydrin and other epoxides, triphosphates, divinyl sulphone, can be used as non-reversible crosslinkers for polysaccharide biopolymers, while dialdehydes, thiol reagents and the like may be used for proteinaceous biopolymers. The crosslinking reaction may be acid- or base-catalysed. The level of crosslinking agent can conveniently be between 0.1 and 10 weight % with respect to the biopolymer. The crosslinking agent may already be present at the start of the mechanical treatment, but in case of a non-pre-gelatinised biopolymer such as granular starch, it is preferred that the crosslinking agent is added later on, i.e. during the mechanical treatment.

The mechanically treated, crosslinked biopolymer is then formed into a latex by dispersion in a suitable solvent, usually water and/or another hydroxylic solvent such as an alcohol), to a concentration of between 4 and 50 weight % especially between 10 and 40 wt. %. Prior to the dispersion a cryogenic grinding step may be performed, but stirring with mild heating may work equally well. This treatment results in a gel which either spontaneously or after induction by water adsorption, is broken into a latex. This viscosity behaviour can be utilised for applications of the particles, such as improved mixing, etc. If desired, the dispersed biopolymer may be further crosslinked, using the same or other crosslinking agents as describe above. The extrudate is characterised by swelling in an aqueous solvent, e.g. water or a mixture of at least 50% water with a water-miscible solvent such as an alcohol, and by exhibiting a viscosity drop afterwards to produce a dispersion of nanoparticles.

International Patent Application Publication No. WO 2008/022127 A2 and its equivalent US Patent Application Publication Number 2011/0042841 A1 describe a process for producing biopolymer nanoparticles in large quantities. US Patent Application Publication Numbers 2010/0143738 A1 describes a process for producing biopolymer nanoparticles conjugative with additives during the extrusion process. These publications are incoporated by reference.

The process can be operated to produce particles that have a number average particle size in the range of 50 to 150 nm and which, considering a distribution of their particle sizes, are also predominantly in the range of 50 to 150 nm in size. Such particles include, for example, EcoSphere® 2202 particles commercially available from Ecosynthetix Inc. of Burlington, Ontario, Canada and EcoSynthetix Ltd. of Lansing, Mich., USA. These products are made primarily from starch including amylose and amylopectin. The product is normally sold for to replace petroleum based latex binders in industrial applications, such as coated paper and paperboard. The product is provided in the form of a dry powder of agglomerated nanoparticles with a volume mean diameter of about 300 microns. When mixed in water and stirred, the agglomerates break apart and form a stable dispersion of the nanoparticles.

Comparing FIG. 2A to FIG. 2B, the EcoSphere® 2202 nanoparticles 10 are about 100 to 300 times smaller than native starch granules 20. Whereas a starch granule 20 may be 15 microns in size, the nanoparticles 10 are clearly well under 200 nm in size. Accordingly, the effective surface area of the nanoparticles 10 is much greater, for example 200 square meters per gram or more.

Figure 4:
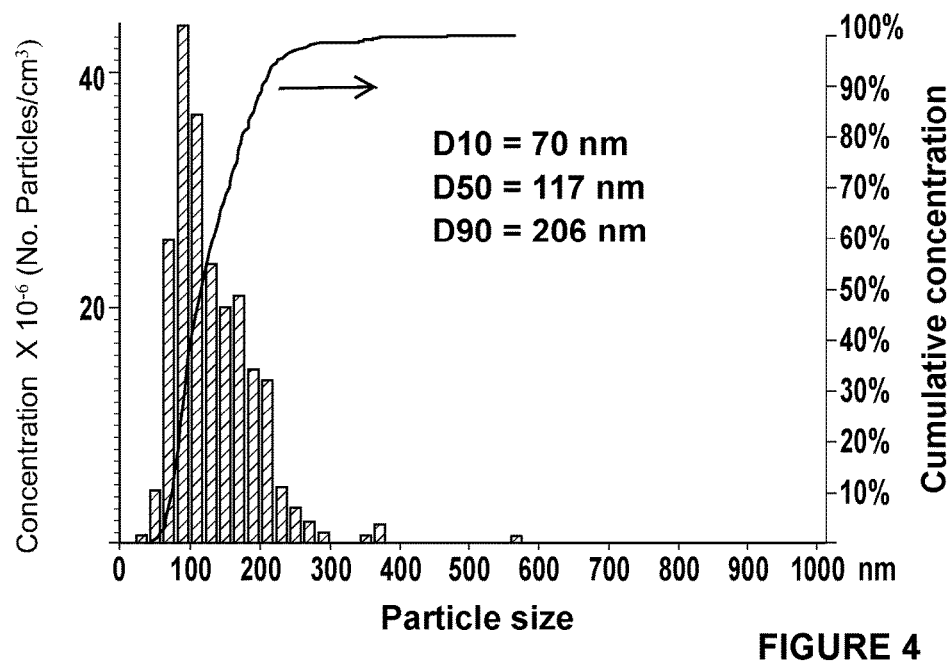
FIG. 4 shows an analysis of particle size for an aqueous dispersion of the cross-linked starch nanoparticles of FIG. 2 by Nanoparticle Tracking Analysis (NTA).

FIGS. 3 and 4 illustrate particle size measurements of an aqueous dispersion of EcoSphere® nanoparticles by Dynamic Laser Light Scattering (DLS) and by Nanoparticle Tracking Analysis (NTA), respectively. These two techniques are complementary, given that the NTA technique is a direct measurement of the diffusion coefficient for individual particles tracked via video tracking software (and relates that to particle diameter via the Stokes-Einstein equation), and can measure particles in the range of 50-1000 nm, while DLS can measure to smaller particle sizes below 50 nm. Other techniques, including oscillating probe Atomic Force Microscopy (AFM), Scanning Electron Microscopy (SEM), Environmental SEM (ESEM), Transmission Electron Microscopy (TEM) and Scanning/Transmission Electron Microscopy (STEM), all provided similar particle size images consistent with the data in FIGS. 3 and 4.

Referring to FIG. 3, most of the particles have a size in the range of about 50 to 100 nm. FIG. 3 also indicates a number of particles apparently having a size of about 10 microns. However, based on other measurements, such as scanning electron microscope photos of freeze dried samples as shown in FIG. 2 and the NTA measuments of FIG. 4, the inventors believe that such larger particles may be over-represented in the sample and that the results may include agglomerations of particles or an anomaly in the DLS measurement. As indicated in the NTA measurements, most of the particles (D50) are under 120 nm in size and there are virtually no particles larger than 400 nm. Any particles larger than 1000 nm would be removed quickly from the body causing no harm but wasting some of an intended dosage of the drug. Accordingly, if a sample includes material amounts of particles over 1000 nm in size, these may be removed by filtration before a drug is loaded into the nanoparticles.

Figure 5:
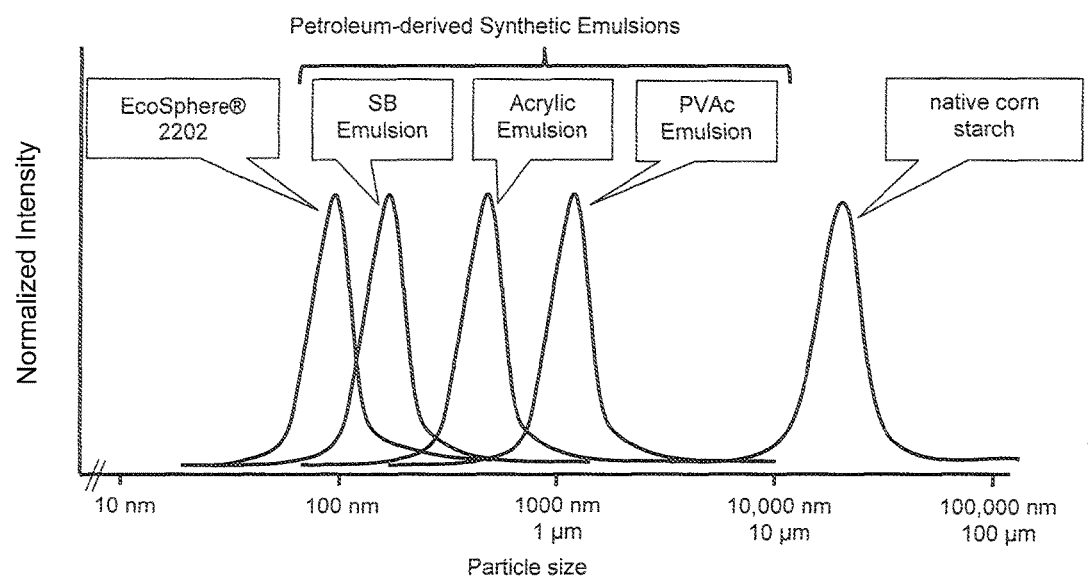
FIG. 5 is a schematic graph comparing particle sizes for the cross-linked starch nanoparticles of FIG. 2, synthetic polymer colloids and native corn starch.

Referring to FIG. 5, the nanoparticles are generally smaller than particles in synthetic latex emulsions The nanoparticles have a narrow size distribution, with a polydispersity index of about 30%, and properties characteristic of polymer colloids. The nanoparticles, since they are predominantly in the size range of about 50 to 150 nm (for example 50% or more of the nanoparticles by number or mass may be in this range), the nanoparticles are cleared more slowly in the systemic system (liver, spleen) than is the case of larger particles. The particles are also hydrophilic, which further inhibits removal in the RES. The degradation products of the starch nanoparticles (D-glucose and maltodextrans) are non-toxic. The additional natural materials and chemicals that are used to make the starch nanospheres are also relatively non-toxic.

The discrete nanoparticles are also not water soluble, but instead form a stable dispersion of swollen hydrogel colloidal crosslinked particles in water.

FIGS. 6A and 6B illustrate that the biobased latex consists of water-swollen crosslinked starch nanoparticles. They de-swell with increasing solids so that their dispersions can be made at higher solids. In contrast, the particles in synthetic latex emulsions do not swell nor contain a substantial portion of water inside the colloid particles. The swelling characteristics of typical SB latex and biolatex colloids have been compared and reported in a number of articles (see Do Ik Lee, Steven Bloembergen, and John van Leeuwen, "Development of New Biobased Emulsion Binders", PaperCon2010, "Talent, Technology and Transformation", Atlanta, Ga., May 2-5, 2010; and, Steven Bloembergen, Edward VanEgdom, Robert Wildi, Ian. J. McLennan, Do Ik Lee, Charles P. Klass, and John van Leeuwen, "Biolatex Binders for Paper and Paperboard Applications", Journal of Pulp and Paper Science, 36, No 3-4, p. 151-161, 2011).

Figure 7:
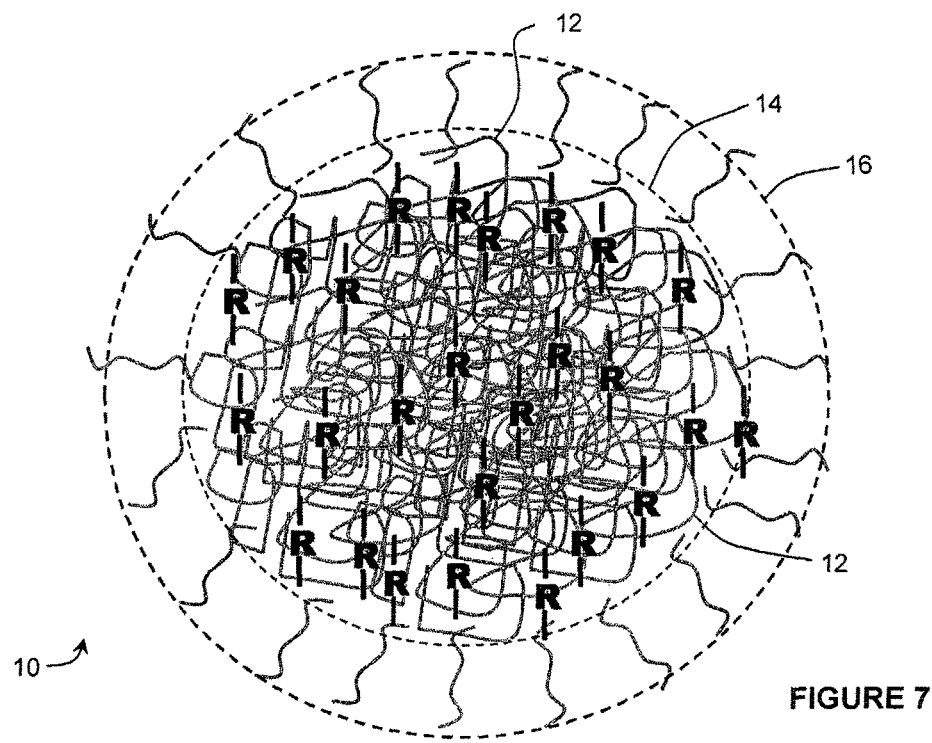
FIG. 7 is a schematic model of the cross-linked starch nanoparticles of FIG. 2.

FIG. 7 illustrates a schematic model for the nanoparticles 10. The nanoparticles 10 can be thought of as one crosslinked macromolecular unit, with —R— representing an intermolecular crosslink between individual polymer 12. Other types of crosslinked structures may exist, such as intramolecular crosslinks. The nanoparticle 10 can be thought of as having a core 14 that takes in and releases water as it swells and de-swells and a shell 16 which provides a steric stabilization mechanism for the colloid particles and through which water is released, bound and adsorbed. The structure of the nanoparticles is further described in Steven Bloembergen, Ian. J. McLennan, John van Leeuwen and Do Ik Lee, "Specialty Biobased Monomers and Emulsion Polymers Derived from Starch", 2010 PTS Advanced Coating Fundamentals Symposium, Munich, Germany, Oct. 11-13, 2010.

Aqueous dispersions of starch nanoparticles have been prepared that are stable for up to 12 months or longer, compared to minutes or hours for cooked solutions of regular corn starch or other starches. Because typical native starches contain very high molecular weight amylopectin polymer (millions of daltons) and high molecular weigth amylose polymer (hundreds of thousands of daltons), their solutions up to 5 or 10% solids have very high gel-like viscosities. Commercial dispersions of corn starch granules typically reach up to about 30% solids or higher, because these products have been chemically, thermally or enzymatically treated to reduce their molecular weight in order to attain higher solids contents. This is the typical molecular weight/solids trade off that one faces to maintain a reasonably low viscosity for polymer solutions. Much higher solids pure dispersions (up to about 40% solids), and ultra-high solids formulations (up to 72% solids) have been developed for EcoSphere® starch nanospheres. This is beneficial for drug delivery applications, where a high solids concentration in a low viscosity dispersion facilitates high drug loadings.

Nanoparticles Conjugated with Active Agents and, Optionally, a Targeting Molecule The nanoparticles may be conjugated with an active agent, for example a drug, or other agent and used as a delivery device. Fluorescence studies indicated that the nanoparticles are taken into the cell nucleus. Without intending to be limited by theory, the transport mechanism is believed to be endocytosis.

As discussed above, the core of the nanoparticles takes in water as it swells. Similarly, small molecules, other drugs, or other agents can be taken up, adsorbed, absorbed or otherwise loaded into the core of the nanoparticles. An example presented further below will describe the encapsulation of doxorubicin in the nanoparticles by a phase separation method (Example 1) and by ethanol precipitation (Example 4). By itself, doxorubicin has been linked to acute cardiotoxicity which limits its use. In other experiments, Carmustine and BCNU (bis(chloroethylnitrosourea)) have been loaded into the nanoparticles.

It can be expected that other methods of drug encapsulation may also be used, and that other drugs and agents can be encapsulated. For example, other chemotherapeutic agents such as Cyclophosphoramide and Camptothecins might be loaded into the nanoparticle and, like doxorubicin, make the nanoparticles useful in the treatment of cancer. The nanoparticles may also encapsulate non-chemotherapeutic agents, such as antisense oligonucleotides, peptides, and cytokines for other therapeutic applications.

After the drug is loaded, the particles can be recovered by lyophilization. This results in a powder of the nanoparticles conjugated with the encapsulated drug. The powder can be mixed with water, or another hydroxylic solution, to disperse the nanoparticles. The drug can be administered to treat a patient in this liquid form, for example orally, by intravenous infusion or injection. Alternatively, the powder can be mixed with a pharmaceutical carrier and made into a solid or gelled product, such as a tablet or capsule. The solid form may be administered in any known manner used for pharmaceutical products, such as orally.

The biopolymers of the nanoparticle may be modified or functionalized through chemical or enzymatic modifications before or after forming the nanoparticle. In principle, any chemical or enzymatic modification known for polysaccharides can be employed. For example, a summary of various chemical and enzymatic oxidation processes is provided in column 1, line 66 to column 3, line 50 in R. A. Jewel et al., U.S. Pat. No. 6,379,494, "Method of Making Carboxylated Cellulose Fibers and Products of The Method", Apr. 30, 2002. Although these methods are discussed in relation to cellulose, many if not all of them are adaptable to starch polymers.

In Example 4, the starch polymers were functionalized after the nanoparticles are formed. In particular, the polymers were oxidized to add carboxyl functional groups. While this is described in Example 4 as relating primarily to the attachment of an aptamer, the functionalization was also shown to facilitate the encapsulation of doxorubicin.

The chemical or enzymatic modification may also involve other types of functionalities introduced onto the biopolymers to provide binding sites for the aptamer, the active agent or both. Surface modification of the nanospheres may also alter their systemic as well as local clearance rates to provide a better control of the delivered therapeutic dose and the targeted delivery, if any. For example, the oxidation resulted in a change in the zeta potential of the nanoparticle. The zeta potential of a non-functionalized nanoparticle is in the range of 0 to negative 6 mv. The oxidized particle had a zeta potential of about negative 25 mV. The oxidation reaction could also be controlled to provide modified nanoparticles having intermediate zeta potential values. Tuning the charge on the nanoparticles will allow selective adsorption of different drugs and agents and in addition provide a way of controlling the release profile. Many small molecules being developed for cancer treatment are hydrophobic and lipophilic, hence difficult to dissolve. Surface modifications of the nanoparticle can enhance the ability of these drugs to be loaded in the core of the nanoparticle.

While the water soluble TEMPO catalyst used in Example 4 provided starch functionalities throughout the crosslinked nanoparticle, an immobilized TEMPO catalyst causes only polymers at the surface of the nanoparticle to be functionalized. This could be used, for example, to attach an aptamer to the nanoparticle with less modification of the zeta potential of the core of the nanoparticle.

While any form of oxidation may be used, the TEMPO oxidation is preferred. The TEMPO catalyst is used to specifically modify the C6 hydroxyl of the glucopyranoside position to a carboxyl functionality. This process prevents the molecular weight reduction of the polysaccharide polymer that is common to many other oxidative processes.

Many functionalization techniques are known to add aldehyde groups to polysaccharide polymers. Without intending to exclude the possibility that one of these functionalization techniques might be useful, they are not currently preferred. The aldehyde groups are reactive and tend to cause the nanoparticles to stick together. This interferes with creating a colloidal dispersion, and so may also interfere with distribution of the nanoparticles in the body.

The zeta potential of unmodified nanoparticles is low, hence their colloidal stability is attributed mainly to steric stabilization. Without being bound by theory, the shell containing short polysaccharide chains which project into the aqueous environment, functions as a colloidal stabilizer for the particle in water and as a partial hydrophilic shell of bound water. This in turn retards the efflux or diffusion of hydrophobic drugs from the particle.

In the examples, the active agent doxorubicin was loaded into the nanoparticles so that the release profile could be followed using a fluorescence technique. This work has demonstrated a biphasic release profile with suitable release kinetics spanning multiple hours of sustained release of the active agent. The fluorescence of the drug loaded nanoparticle declines but some fluorescence remains even after 12 hours. This indicates that not all of drug releases from an intact particle. The remainder of drug, however, will be released in the body as the particle degrades, for example due to alpha-amylase enzymes in body. The complete release time may be near 24 hours.

In animal studies described in Example 3, doxorubicin loaded nanospheres were used to treat glioblastoma multiforme, a primary brain tumor in athymic mice. These studies demonstrated a 30% increase in survival for the mice treated with doxorubicin-loaded nanospheres relative to the appropriate controls. Without intending to limit the invention to any particular theory, this success is attributed to one or more of several factors including the size of the nanoparticles, the surface properties of the nanoparticles, and the release kinetics of the nanoparticles, for example the sustained release of the drug from the nanoparticles. The encapsulated doxorubicin is believed to enter the cell via endocytosis due to the relatively small size of the nanoparticle, while the free drug is metabolized and excreted.

Figure 11:
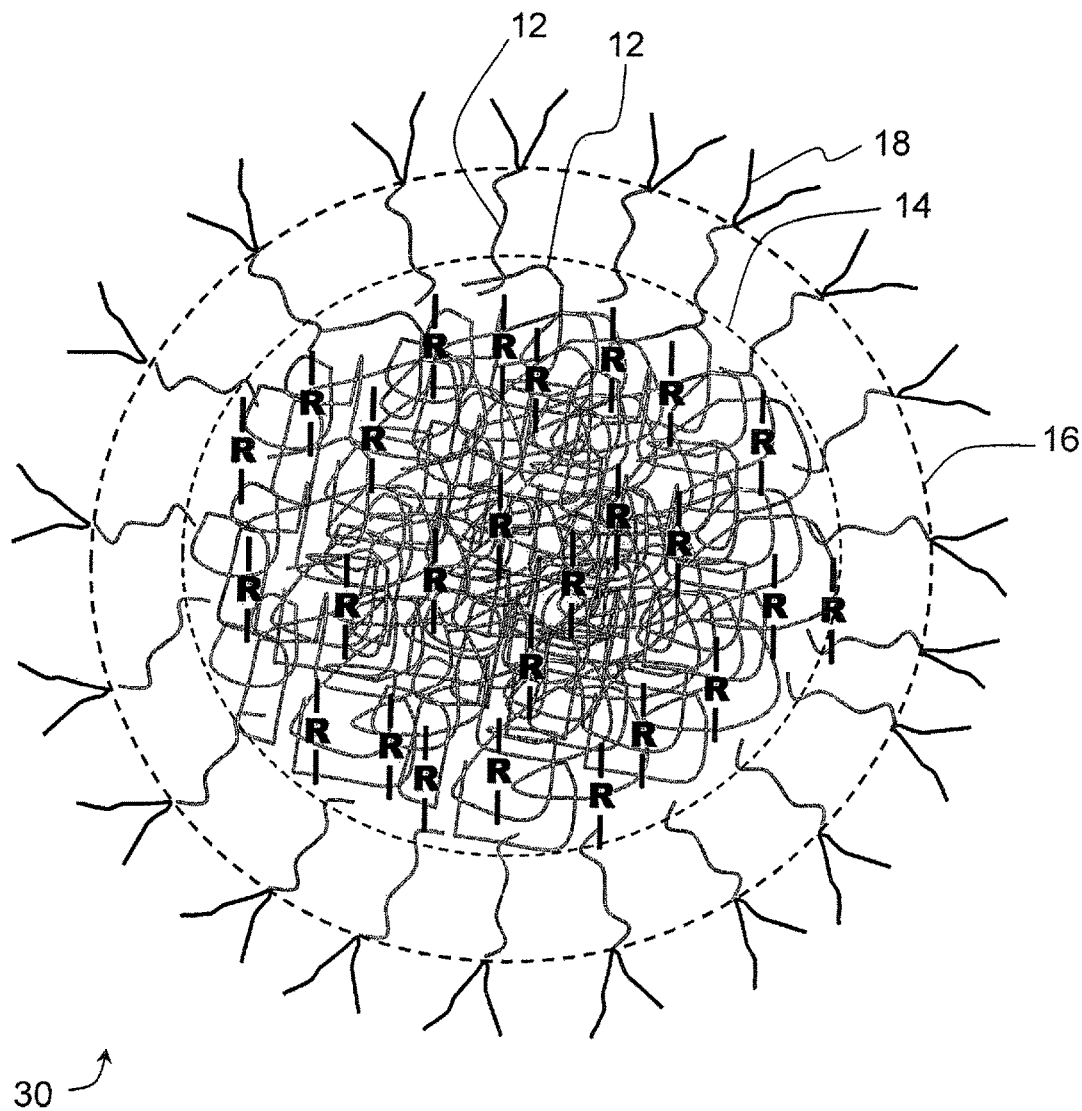
FIG. 11 is a schematic model of a cross-linked starch nanoparticle of FIG. 2 conjugated with a drug and an aptamer.

FIG. 11 shows a bioconjugate device 30 having an aptamer 18, a polymer 12 and an active agent, not separately shown but provided within the core 14. The bioconjugate device 30 may be used for the delivery of therapeutically effective amounts of the active agent to targeted cells for the treatment of specific disorders. The bioconjugate device 30 may be made by making a chemical or enzymatic modification to a biocompatible or resorbable colloidal polymer hydrogel, encapsulating an active agent within the colloidal polymer hydrogel, and modifying the surface of the hydrogel by attaching an aptamer onto it. The aptamer 18 typically has a size of less than about 10 nm and increases the diameter of the bioconjugate device 30 by only about 20 nm or less. Optionally, other targeting ligands or other molecules might also be used.

Aptamers are capable of binding to a target molecule that are located in a specific site which may include cancer cells. For example, AS1411 has been shown to bind to nucleolin (Soundararajan et al., "Plasma Membrane Nucleolin Is a Receptor for the Anticancer Aptamer AS1411 in MV4-11 Leukemia Cells", *Molecular Pharmacology*, Vol. 76, No. 5, 2009). Binding to nucleolin receptors is useful in the treatment of a wide array of cancers such as renal cell carcinoma, breast cancer, prostate cancer and others. AS1411 may also be tagged with, for example, a Cy3 fluorescent tag for imaging purposes.

Another potentially useful aptamer is sgc4. This aptamer was developed by way of the SELEX process from T-cell leukemia cell lines and is able to recognize leukemia cells (Shannguan et al., "Aptamers Evolved from Cultured Cancer Cells Reveal Molecular Differences of Cancer Cells in Patient Samples", *Clinical Chemisty* 53, No.6, 2007). However, sgc4 has a short biological life if it is not conjugated. Its sequence is described in US Patent Publication 2009/0117549. Shorter variants of the sequence may also be effective. Sgc8c aptamers have also been reported to be useful for targeting leukemia cells (Ozaip et al., *Pharmaceuticals* 2011, 4, 1137-1157)

Aptamers having an amine modification on the 3' end of the DNA can be linked, for example by one or more covalent bonds, to the carboxyl groups of the functionalized nanoparticle. The linkage may be made, for example, using EDC chemistry, or by another linkage between the carboxyl and the amine. An example of such a linking using an amine modified test strand of DNA is described in Example 4. Similarly, aptamers such as AS1411 and sgc4 which can also be provided with an amine modification should also link to the nanoparticle. When also loaded with an active agent such as doxorubicin, the resulting aptamer-polymer-active agent bioconjugate device will be adapted to deliver therapeutically effective amounts of an active agent to targeted leukemia or other cancer cells.

By using an immobilized TEMPO as the catalyst to oxidize the starch and form carboxyl groups, activation of the carboxyl group by NHS and EDC will allow for the binding of an amine-modified aptamer to the surface of the polymer colloid, thereby forming a covalent linkage. The number of functional groups on the surface of the nanoparticle may determine the aptamer surface density.

TEMPO (2,2,6,6-tetramethylpiperidine-1-oxyl radical) reacts with the hydroxyl groups on the starch polymers in an aqueous medium to create the desired carboxyl groups (—COON) by the process known as TEMPO-mediated carboxylation. NaBr is used to stabilize this reaction. Hypochlorite (NaClO) initiates the reaction by keeping the pH at 10.2-10.5. Then HCl can be used to lower the pH and reprotonate the carboxyl groups. 1-Ethyl-3-(3-dimethylaminopropyl)carbodiimide hydrochloride (EDC) and N-hydroxysuccinimide (NHS) are chemicals which can act as coupling agents to form carboxyl-amino covalent linkages, which link the carboxylated starch nanoparticle to the 3'-amine-modified ssDNA aptamer.

The following examples serve to illustrate one or more parts of one or more inventions and are not intended to limit any claim.

EXAMPLE 1

Incorporation of Fluorescent Agents into Starch Based Nanoparticles

Incorporation of two compounds, in particular the fluorescent model compound Calcein and the fluorescent anticancer agent doxorubicin (IUPAC Name: (7S,9S)-7-[(2R, 4S,5S,6S)-4-amino-5-hydroxy-6-methyloxan-2-yl]oxy-6,9, 11-trihydroxy-9-(2-hydroxyethyl)-4-methoxy-8,10-dihydro-7H-tetracene-5,12-dione; commercial products include Adriamycin™ and Doxil™), into biopolymer nanoparticles (EcoSphere® 2202 from EcoSynthetix Inc.) was accomplished by a phase separation technique. This technique involves the formation of a water-in-oil emulsion. In a 250 mL round bottom flask, the starch based nanoparticles were dispersed at <5% solids (wlw) in water under mechanical agitation at a pH of about 10 using dilute caustic. The resultant dispersion was titrated to a pH of 7 using dilute hydrochloric acid. The substance to be incorporated in the nanosphere colloid matrix (calcein or doxorubicin) was dissolved in the dispersion containing the biopolymer nanoparticles. The amount of encapsulated active agent prepared ranged from 0.04%-0.4% (w/w). The flask was placed inside an insulated container and secured properly. The solution was then stirred for several minutes. Hexane was added dropwise under continuous agitation until an emulsion was formed. The emulsion was immediately frozen using liquid nitrogen. The flask was connected to a vacuum system and lyophilization was carried out at −85° C. After 24 hours, when the vacuum gauge indicated no further vapor removal, the dried sample was removed from the vacuum system and stored at −10° C.

EXAMPLE 2

Drug Release Studies

Figure 8:
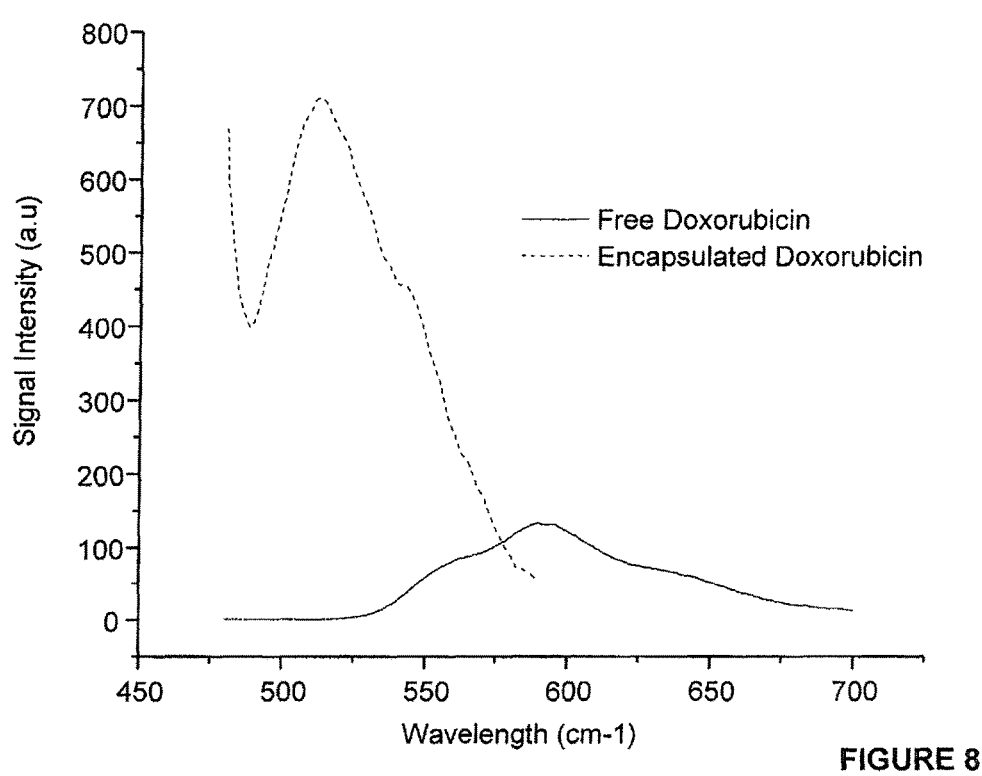
FIG. 8 is a chart showing the fluorescence spectrum of free doxorubicin and doxorubicin entrapped in the cross-linked starch nanoparticles of FIG. 2.
Figure 9A:
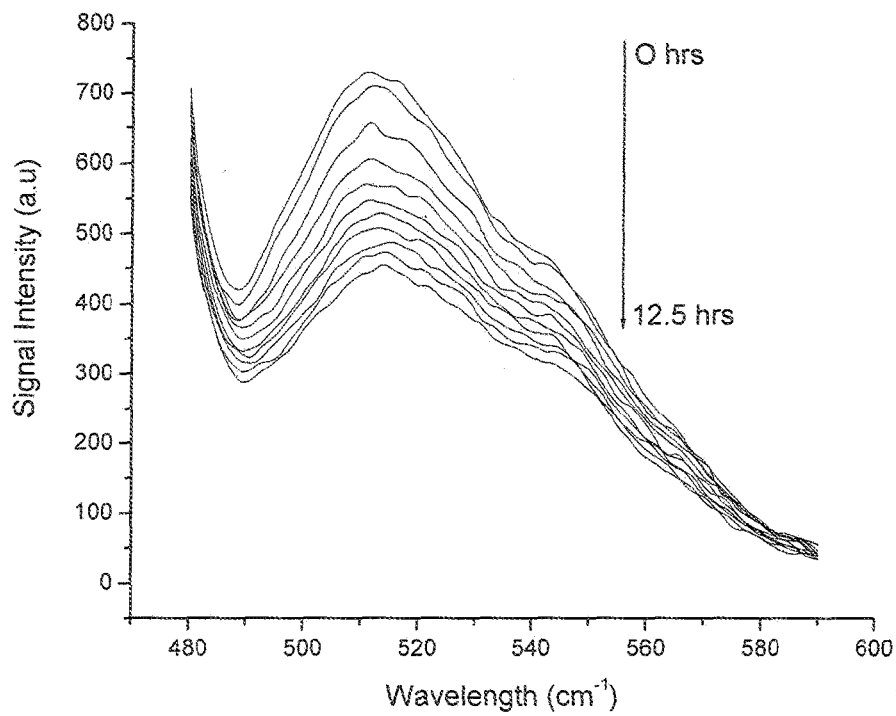
FIG. 9 is a chart showing a release profile of doxorubicin from the cross-linked starch nanoparticles of FIG. 2.
Figure 10A:
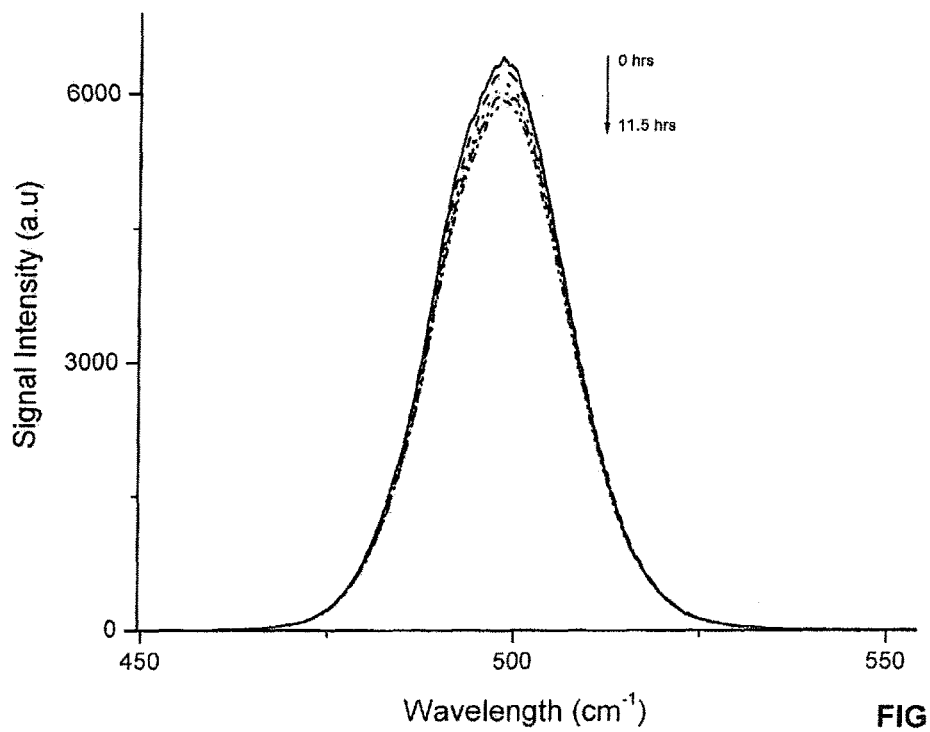
FIG. 10 is a chart showing the fluorescence spectrum of Calcein and a release profile of Calcein from the cross-linked starch nanoparticles of FIG. 2.

The use of fluorescent dyes as spectral probes to investigate inclusion complexation is known (see Saenger, W. *Angew. Chem.* 1980, 92, 343-61 and Wenz, G. *Angew. Chem.* 1994, 106, 851-70). This approach was adopted in studying the efficacy of starch based nanoparticles (in this example we used EcoSphere® 2202 from EcoSynthetix Inc.) to encapsulate selected drugs and the ability of this material to release the drug over time. Fluorescent compounds such as calcein and doxorubicin are very sensitive to environmental changes. The fluorescent signal of the molecules was enhanced when it was incorporated into the matrix of starch based nanoparticles. As shown in FIG. 8, the signal intensity of free doxorubicin is much lower than that of the encapsulated doxorubicin. In addition, a significant hypsochromic shift (change of spectral band position in the emission spectrum of a molecule to a shorter wavelength) is observed when doxorubicin is encapsulated. FIG. 9A shows a series of fluorescence spectra of doxorubicin obtained as a function of time. It can be seen that there is a significant decrease in signal intensity with time, indicating sustained release of the active agent. In addition, there was a relatively small bathochromic shift (change of spectral band position in the emission spectrum of a molecule to a shorter wavelength) observed. Without intending to be limited to any theory of operation, it appears that the reduced shift indicates a biphasic release mechanism given that not all of the active agent was released over the course of the 12 hour experiment. FIG. 10A shows a series of fluorescence spectra of calcein obtained as a function of time. It can be seen that there is a decrease in signal intensity with time, indicating sustained release of the active agent.

occurred in individuals in which several doses of doxorubicin loaded nanoparticles were administered. Table 1 demonstrates the efficacy as well as the safety of the doxorubicin loaded biopolymer nanoparticles in treating a primary human brain tumor in athymic mice.

TABLE 1

In vivo studies of human xenographs implanted in athymic mice

| Dose × Conc. (w/w) | 1 × 0.03% (Dox-nano) | 1 × 0.5% (Dox-nano) | 1 × 0.5% (Dox-nano) | 2 × 0.5% (Dox-nano) | 4 × 0.5% (Dox-nano) | 4 × 0.5% (Dox-nano) | 1 × 2% (Dox-nano) | Free Dox Control |
|---|---|---|---|---|---|---|---|---|
| Drug dose | 0.075 mg/kg | 1.25 mg/kg | 1.25 mg/kg | 2.5 mg/kg | 5 mg/kg | 5 mg/kg | 5 mg/kg | 5 mg/kg |
| T-C(days) | 0.99 | 4.8 | 5.31 | 8.09 | 7.56 | 6.57 | 2.44 | 1.53 |
| P value | 0.14 | 0.14 | 0.14 | 0.04 | 0.001 | 0.012 | 0.03 | 0.32 |
| Regressions | 2/8 | 2/8 | 0/10 | 0/10 | 2/9 | 0/9 | 2/8 | 0/10 |
| Toxic deaths | 0/8 | 0/8 | 0/10 | 0/10 | 2/9 | 0/9 | 0/8 | 0/10 |

The following abbreviations are used in Table 1:
"Dox" = doxorubicin;
"Dox-nano" = doxorubicin encapsulated starch based nanoparticles.

Figure 9B:
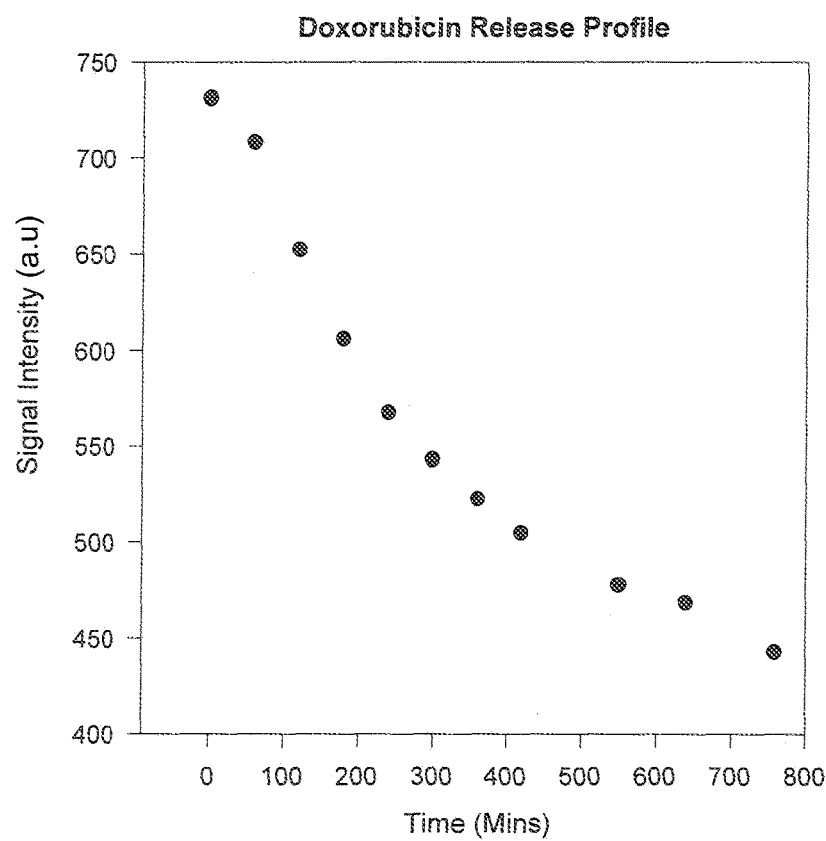
Figure 10B:
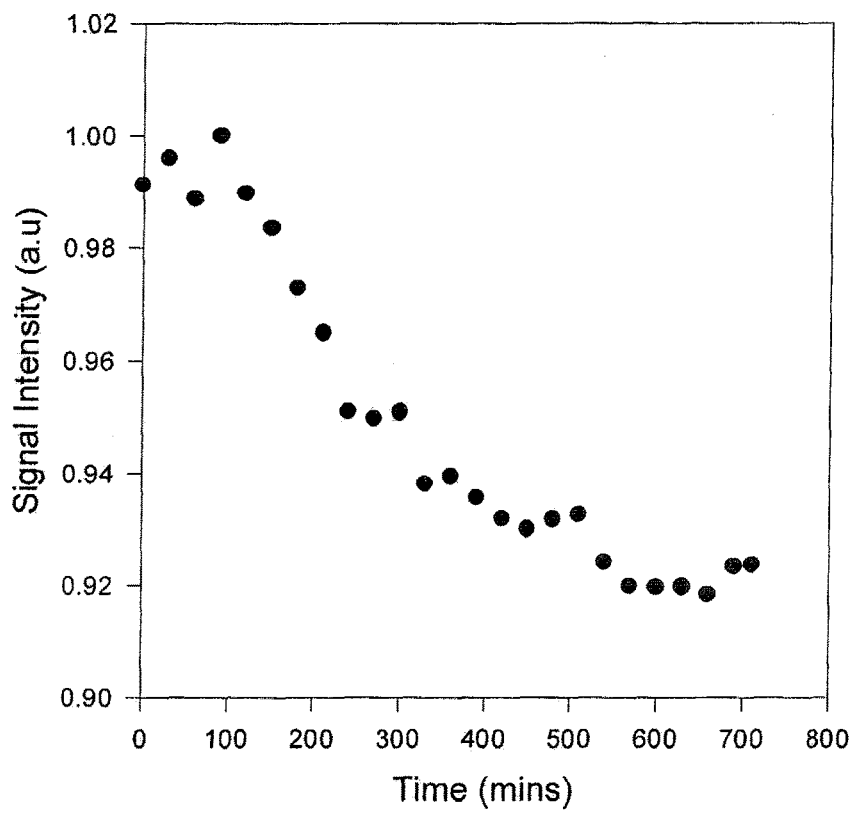

The data shown in FIGS. 9A and 10A illustrate that enhancement in signal intensity for calcein and doxorubicin due to inclusion complexation with the starch based nanoparticles can be used to monitor the release of the active agents. FIGS. 9B and 10B are plots of signal intensity as a function of time at the maximum signal intensity of the fluorescence emission spectra for doxorubicin and calcein, respectively. These data show that the concentration of fluorophore molecules inside the supramolecular cavity is changing with time. The release of the molecules appears to be proportional to the concentration gradient of the active agents. The sustained release of active agents from the biopolymer nanoparticles extended to more than 10 hours. The results demonstrate that the biopolymer nanoparticles provide a stable matrix for the steady release of active agents over an extended time period. The release mechanism appears to be predominantly diffusion controlled.

EXAMPLE 3

In Vivo Studies of Human Xenographs Implanted in Athymic Mice

In order to demonstrate the efficacy of the starch based nanoparticles as a drug delivery device, they were loaded with the anticancer drug doxorubicin as described in Example 1. The doxorubicin loaded nanoparticles were administered to athymic mice which had a human xenograph of a primary brain tumor (D 245 glioblastoma multiform) previously grown at a subcutaneous site. Athymic mice were chosen for these studies because normal mice are capable of immunologically rejecting implanted foreign xenographs, specifically human tumors. The animals (both control and treated) were monitored for tumor regression and survival. The results of the study are presented in Table 1.

The procedure consisted of inoculation of a tumor brei into a subcutaneous site in athymic mice. The subcutaneous tumors were grown to approximately 200 cubic millimeters in size (6-8 mm in diameter). Subsequently, either the free drug or the drug loaded nanoparticles were injected at the tumor site or i.p. (intra peritoneal). Typically it took approximately 20 days for the animals to test out. The animals were treated in groups of 8 to 10 individuals. The highest survival rates (highest T-C values or increased life span in days)

Dispersions were 100 mg nanospheres/5 mL saline (1×0.5% Dox-nano), 200 mg nanospheres/5 mL saline (2×0.5% Dox-nano) or 400 mg nanospheres/5 mL saline (4×0.5% Dox-nano).

Injections were each 0.25 mL/20 gram mouse (all single injections).

T-C is defined as: Average of (days lived by drug-treated animal minus days lived by control animals); i.e., increased life span in days.

The Control was provided as follows: Varied—Untreated mice injected with saline; Untreated mice; Mice treated with drug-free nanospheres (100 mgs/5 mL saline).

P value: Test run for significance. P values are calculated using non-parametric statistical method by Hollander and Wolfe.

Regressions: Indicate that tumors drop below previous measurement and stay below for 2 consecutive measurements.

EXAMPLE 4

Conjugating a Ligand

The nanoparticle may be conjugated to a ligand specific for a tumor, metastatic cancer cell, or other targeting tissue or organ. This capability was demonstrated by the following procedures and tests.

Oxidation of EcoSphere

Various different types of functionalities may be introduced onto the starch based nanoparticles to provide binding sites for the aptamer as well as the active agent. As described in the Detailed Description, various chemical modification techniques can be employed. A particularly useful chemical modification is oxidation of starch to produce carboxyl functionalities. To illustrate this, TEMPO-mediated oxidation was carried out for both the starch based nanoparticles (EcoSphere® 2202 from EcoSynthetix Inc.) as well as for regular native (unmodified) corn starch. In this method, starch was oxidized with sodium hypochlorite (NaClO) and 2,2,6,6-tetramethylpiperidin-1-oxyl (TEMPO) radicals, at temperatures between 0 and 4° C. and pH of 10.8. The degree of oxidation was controlled by amount of NaClO added. As noted, two types of starch were used. The first was EcoSphere starch based nanoparticles and the second one was regular corn starch purchased from Sigma-Aldrich. The procedures were as described below.

In a glass jar, 4 g of EcoSphere and 80 mL MilliQ water were added and mixed thoroughly to create a ~5% dispersion. In a second jar 4 g of Corn Starch and 80 mL of MilliQ water were added to create a ~5% solution. The second jar was heated up to above 80° C. (max 95° C.) under agitation and allowed to fully dissolve. Subsequently it was cooled to room temperature. Separately, in two 45 mL tubes 40 mL of water, 38 mg TEMPO, and 508 mg NaBr were added into each tube (0.01 mol TEMPO per anhydroglucose unit of starch; 0.2 mol NaBr per anhydroglucose unit of starch), stirred until fully dissolved, and cooled for 30 minutes in an ice batch. Next the content of one tube was mixed into each jar. A pH measurement was taken, which initially was 3.8 for the EcoSphere jar and 7.4 for the Corn Starch jar. Next 450 µL of 0.5 M NaOH was added to the EcoSphere jar to reach pH 10.75, and 200 µL of 0.5 M NaOH was added to the Corn Starch jar to reach pH 10.75. Subsequently, 10 mL of NaClO was added when the pH dropped to around 6-7, and pH measurements were taken every 10-15 min. As the mixtures continued to stir and the pH dropped, the color became darker (yellow/orange). A total of 60 mL NaClO was added and the pH was finally adjusted to 8.0 before the oxidized starch was diluted 1:1 with ethanol. Ethanol precipitated the modified EcoSphere nanoparticles and modified starch and they were harvested by centrifugation and washed by water and ethanol and finally dried by lyophilization (freeze-drying).

The oxidized EcoSphere was characterized by zeta-potential measure and dynamic light scattering. Zeta measurement showed that the modified particles carried a negative charge with zeta-potential of −25.5 mV, while unmodified particles were essentially neutral. The size of the particles appeared to be slightly smaller compared to the non-oxidized ones (i.e. the NTA Mode was 113 versus 141 nm).

The color of the final product depended on the pH of the solution after oxidization. If the pH was too high (higher than 10), a yellow colored product was obtained. It was found that this color can be removed by lowering the pH.

DNA Attachment

Subsequently, amino-modified and fluorescently labeled DNA was attached to the starch nanoparticles using N-(3-Dimethylaminopropyl)-N'-ethylcarbodiimide hydrochloride (EDC) as a coupling agent. The reaction mixture contained 5 µM FAM (6-carboxyfluorescein) and amino dual labeled DNA, 1-5% COOH-modified starch, 20 mM 2-(N-morpholino)ethanesulfonic acid (MES) buffer, pH 6.0 and 20 mM freshly prepared EDC was added the last. Agarose gel electrophoresis was carried out for DNA and DNA-conjugated to TEMPO-oxidized EcoSphere nanoparticles. It was found that the gel fluorescence intensity was more evenly distributed and some of the DNA migrated more slowly, indicating conjugation to the starch nanoparticles. In some of the alternative DNA attachment protocols the carboxyl groups on starch were first activated using N-Hydroxysuccinimide (NHS) at 5 mM (¼ of the amount of EDC) for 15 minutes before adding the DNA. Next this mixture was allowed to react for several hours. Without intending to be bound by any particular theory of operation, NHS may help to facilitate the EDC linking reaction by activating carboxyl groups so it can react with an amine to form an amide, rather than a salt with an amine.

Thus the DNA used in this example, which served as a model compound for ligand attachment, was successfully attached. The DNA sequence was 5'-FAM-ACG CAT CTG TGA AGA GAA CCT GGG-NH$_2$-3'.

Attachment of an Aptamer

An aptamer was attached to EcoSphere® 2202 particles using the procedure described above. Attachment of the aptamer was confirmed by laboratory observations of nanoparticle fluorescence. The aptamer was, AS1411, which is believed to have (as modified) the sequence: 5-Cy3-TTG-GTGGTGGTGGTTGTGGTGGTGGTGG-NH$_2$-3' (i.e. AS1411 aptamer with Cy3 fluorescent tag and amine group). The fluorescent tag, used for imaging purposes in the diagnostic gel electrophoresis test, can of course be omitted if needed. However, an additional purpose for the fluorescent tagging is to facilitate monitoring of the binding and uptake of the modified nanoparticles by a cell. As for the DNA described above, the aptamers had an amine modification on the 3' end of the DNA so that it could be linked using EDC chemistry to carboxyl functionalities on the nanoparticle.

Four 200 microliter wells were prepared with cells of an ovarian cancer cell line (HeLa) and given time to culture and grow. Well 1 was left with only the HeLa cells. Well 2 had unconjugated AS1411 added to it. Well 3 had EcoSphere® 2202 nanoparticles with conjugated AS1411 added to it. Well 4 had nanoparticles conjugated with a control sequence added to it. The control sequence has no known affinity for HeLa cells. The wells were then allowed to culture for a further 48 hours.

After the 48 hours had elapsed, cells from the wells were washed to remove any fluorescent marks on any unbound particles external top the cells. The cells were then observed under a fluorescence microscope. Fluorescent marks were observed within the cells of well 3 confirming that the nanoparticle/aptamer conjugate had been taken into the cells.

Drug Adsorption and Release Studies

In a dilute aqueous dispersion (e.g. 1-5%) the EcoSphere nanoparticles are highly swollen and their density is close to that of water. As a result, centrifugation and even ultracentrifugation were ineffective methods to separate the particles from the aqueous dispersion media. Instead, drug loading was evaluated by way of fluorescence change. It was found that the adsorption of the anticancer drug doxorubicin (Dox) was very much improved after modification of the EcoSphere nanoparticles with carboxylate groups. Upon adsorption, the fluorescence of Dox was also quenched by the carboxylated EcoSphere. This was clearly visible under the 245 nm excitation in a dark room using a handheld UV lamp. The fluorescence quenching provides an analytical method to monitor Dox adsorption.

To ensure that the observed quenching was not due to a pH effect, the fluorescence was subsequently compared for the following: Dox was dissolved at a final concentration of 0.01 mg/mL in unmodified EcoSphere, COOH-modified EcoSphere and buffer (no EcoSphere). For each condition, two pH conditions were tested to contain either 20 mM sodium acetate buffer (pH 5.0) or 20 mM 4-(2-hydroxyethyl)-1-piperazineethanesulfonic acid (HEPES) buffer, pH 7.6. The final pH was confirmed to be at the intended values.

Free Dox fluorescence was strong in both pH 5 and 7.6 in water. Mixing with 1% unmodified EcoSphere nanoparticle dispersion induced about 50% fluorescence quenching but mixing with a COOH-modified EcoSphere nanoparticle dispersion completely quenched the fluorescence. This confirmed that COOH-modified EcoSphere is better at adsorbing Dox. Without intending to be bound by any particular theory of operation, this is likely due to electrostatic interactions with the positively charged Dox. Therefore, tuning the EcoSphere charge will allow selective adsorption of various drugs and in addition provide a way of controlling the release profile.

Electrokinetic Measurements

To evaluate the presence of electrostatic charges on the surface of the particles, the zeta potential of the biopolymer nanoparticles and TEMPO oxidized biopolymer nanoparticles was determined from the analysis of the electrokinetic measurements using a Brookhaven ZetaPlus instrument. The cross-linked starch particles were suspended in a solution of NaCl ranging from 0.001 M to 0.1 M concentration, and their electrophoretic mobilites were determined. The electrophoretic mobilities were converted to zeta ($\zeta$) potentials using the Smoluchowski expression, which assumes small particles and dilute ion concentration. The zeta potential of the un-modified starch based nanoparticles was determined to be close to zero, whereas the zeta potential of the TEMPO modified biopolymer nanoparticles was determined to be −25 mV which indicates negatively charged nanoparticles.

Particle Size Analysis

The particle size of dispersed starch based nanoparticles and the TEMPO modified nanoparticles was determined by Nanoparticle Tracking Analysis (NTA) using an LM 20 tracking analysis device (NanoSight Ltd.) equipped with a blue laser (405 nm). The device uses a 50 mW laser operating in the CW mode to illuminate the particles. The light scattered by the particles is captured using a digital camera and the motion of each particle is tracked from frame to frame using NanoSight software. A high speed video is obtained (30 frames per second, average video about 30 s). The trajectories of individual particles are generated from the video sequence and the mean squared displacement determined for each particle. Typically at least 20 trajectories are acquired and 250 to 500 sets of trajectories (each set corresponding to an individual particle) are accumulated in a video sequence. The analysis of the mean squared displacement is used to calculate the diffusion coefficient and the hydrodynamic radius ($r_h$) is determined using the Stokes-Einstein equation. Thus, the diameter of each particle in the sample can be determined and a true particle size distribution derived. Because a diffusion coefficient is obtained for each particle in the field of view, a particle size distribution can be obtained which does not assume a particular mathematical model as in dynamic laser light scattering (DLS) analysis.

Dispersions of biopolymer nanoparticles were prepared using the following procedure: 1) dry agglomerate EcoSphere® powder was mixed in water containing 0.4 wt % sodium carbonate ("lite soda ash") based on dry weight in a Silverson high shear mixer for 15 minutes; the final concentration of the dispersed biolatex ranged from 0.015 to 0.030% (w/w); 2) this dispersion was heated to 45° C. for 15 minutes in a water bath prior to measurement to ensure the agglomerate particles were fully dispersed into nanoparticles.

The above description and attached figures are intended to illustrate at least one embodiment of each claim and not to limit any invention. The invention is defined by the following claims.

We claim:

1. A targeted delivery device comprising,
   a) an aqueous dispersion of discrete biocompatible or resorbable hydrogel nanoparticles, wherein the hydrogel nanoparticles are formed of waxy corn starch polymer molecules connected to each other with intermolecular crosslinks and oxidized to add carboxyl groups to the waxy corn starch polymer molecules; b) an active agent adsorbed within the waxy corn starch polymer molecules; and, c) an amine modified aptamer linked to the carboxyl groups of the waxy corn starch polymer molecules,
   wherein biopolymers of the device consist of starch and the aptamer, wherein the starch does not include dextran or dextrin.

2. The device of claim 1 wherein the surface of the hydrogel nanoparticles is oxidized by way of TEMPO-mediated carboxylation.

3. The device of claim 2, wherein the waxy corn starch is plasticized using shear forces while a cross-linking agent is present.

4. The device of claim 1, wherein the hydrogel nanoparticles have a zeta potential of less than negative 10 mV.

5. The device of claim 1, which is lyophilized.

6. The device of claim 1, wherein the aptamer is coupled to the hydrogel nanoparticles using N-(3-Dimethylaminopropyl)-N'-ethylcarbodiimide hydrochloride.

7. The device of claim 6, wherein the aptamer comprises DNA.

8. The device of claim 1, wherein the active agent comprises a chemotherapeutic drug.

9. The device of claim 8, wherein the chemotherapeutic drug is doxorubicin ((7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8, 10-dihydro-7H-tetracene-5, 12-dione), cyclophosphoramide ((RS)-N,N-bis(2-chloroethyl)-1, 3,2-oxazaphosphinan-2amine 2-oxide) or carmustine (N, N'-bis(2-chloroethyl)-N-nitroso-urea).

10. The device of claim 9, wherein the chemotherapeutic drug is doxorubicin.

11. The device of claim 1, wherein the active agent is loaded into the hydrogel nanoparticles.

12. The device of claim 1, wherein the aptamer comprises DNA.

13. The device of claim 1, wherein the hydrogel nanoparticles are internally crosslinked with a reversible crosslinker.

* * * * *